United States Patent [19]
Kodas et al.

[11] Patent Number: 6,051,257
[45] Date of Patent: Apr. 18, 2000

[54] POWDER BATCH OF PHARMACEUTICALLY-ACTIVE PARTICLES AND METHODS FOR MAKING SAME

[75] Inventors: Toivo T. Kodas; Mark J. Hampden-Smith; James Caruso; Quint H. Powell; Daniel J. Skamser, all of Albuquerque, N.Mex.

[73] Assignee: Superior MicroPowders, LLC, Albuquerque, N.Mex.

[21] Appl. No.: 09/030,054

[22] Filed: Feb. 24, 1998

Related U.S. Application Data

[60] Provisional application No. 60/038,261, Feb. 24, 1997.

[51] Int. Cl.[7] ...................................................... A61K 9/14

[52] U.S. Cl. .......................... 424/489; 424/490; 424/491; 424/499; 514/951

[58] Field of Search ..................................... 424/489, 493, 424/494, 46, 490, 499, 491; 514/951

[56] References Cited

U.S. PATENT DOCUMENTS

| | | |
|---|---|---|
| 4,023,961 | 5/1977 | Douglas et al. . |
| 4,649,911 | 3/1987 | Knight et al. . |
| 5,049,388 | 9/1991 | Knight et al. . |
| 5,269,980 | 12/1993 | Levendis et al. . |
| 5,439,502 | 8/1995 | Kodas et al. . |
| 5,523,065 | 6/1996 | Stangle et al. . |
| 5,743,251 | 4/1998 | Howell et al. . |

*Primary Examiner*—Thurman K. Page
*Assistant Examiner*—Brian K. Seidleck

[57] ABSTRACT

Powder batches of pharmaceutically-active particles and methods for making same. The pharmaceutically-active particles have a small particle size and a narrow particle size distribution and are particularly useful in devices such as medical inhalers. The present invention also provides an aerosol-based method for producing pharmaceutically-active particles wherein an aerosol is produced having a tightly controlled droplet size to produce pharmaceutically-active particles having a small particle size and narrow particle size distribution.

7 Claims, 27 Drawing Sheets

102 → AEROSOL GENERATOR 106 —108→ FURNACE 110 —112→ PARTICLE COLLECTOR 114 →116

102 → 104 ↓ → AEROSOL GENERATOR 106 —108→ FURNACE 110 —112→ PARTICLE MODIFIER 360 —362→ PARTICLE COLLECTOR 114 —116→

FIG.36

POWDER BATCH OF PHARMACEUTICALLY-ACTIVE PARTICLES AND METHODS FOR MAKING SAME

REFERENCE TO RELATED APPLICATION

This application claims priority from U.S. Provisional application Ser. No. 60/038,261, filed Feb. 24, 1997, entitled "PHARMACEUTICAL COMPOSITIONS AND METHODS FOR MAKING SAME", which is incorporated herein by reference in its entirety.

BACKGROUND OF THE INVENTION

1. Field of the Invention

The present invention relates to pharmaceutical compositions in the form of dry powders and methods for making such pharmaceutical compositions. In particular, the present invention is directed to pharmaceutical compositions in the form of fine powders having small size and a narrow size distribution and methods for making such powders.

2. Description of Related Art

There is an increasing desire in the pharmaceutical industry for systems capable of delivering pharmaceuticals to a patient without the use of needles or other devices which are often considered unpleasant or inconvenient by the patient.

One such system that has been utilized is an aerosol delivery system. An aerosol delivery system introduces a predetermined amount of a liquid pharmaceutical into the lungs of a patient in the form of liquid droplets. Such a device is described, for example, in U.S. Pat. No. 4,484,577 by Sackner et al.

It has also been proposed to introduce solid particles of a pharmaceutical composition into the lungs of a patient to deliver the pharmaceutical to the patient's bloodstream. Devices for delivering the powder to the patient's lungs are commonly referred to as dry powder inhalers. Such devices mix a controlled amount of a dry pharmaceutical powder with a gas, usually air, and delivers the dosage to the patient as the patient inhales. Such a device is described, for example, in U.S. Pat. No. 5,492,112 by Mecikalski et al., U.S. Pat. No. 5,351,683 by Chiesi et al. and U.S. Pat. No. 5,320,714 by Brandel, each of which is incorporated herein by reference in its entirety.

Despite the potential advantages of dry powder inhalers, their use has been limited due to a need for improved pharmaceutical powders. Due to the stringent requirement that the dry powder inhaler administer the proper dose of the pharmaceutical, it is generally necessary that the powders have the following properties: high purity; small particle size; narrow particle size distribution; controlled surface chemistry; controlled aerodynamic diameter; and minimal agglomeration. See Broadhead et al., *Drug Development and Industrial Pharmacy*, 18, 1169 (1992).

The most common method for producing powders of pharmaceutical compositions is referred to as spray-drying. Spray drying of pharmaceutical powders is typically used to form dry powders which can be stored for later use, e.g. later dissolution into a liquid, or for tableting or encapsulation in a pill form. See, for example, U.S. Pat. No. 4,830,858 by Payne et al. The spray drying method is described, for example, in the article "Spray-Drying as a Preparation Method of Microparticulate Drug Delivery Systems: An Overview", Giunchedi et al., *STP Pharma Sciences*, 5 (4) pgs. 276–290 (1995). However, most spray-drying methods have not been capable of producing particles that are well-suited for dry powder inhalation. Current spray drying techniques typically produce powders having a wide particle size distribution. Further, spray-drying methods have not produced particles having an average particle size which is desirable for dry powder inhaler devices, such as around 2 $\mu$m. Therefore, the particles must be mechanically milled, which adversely affects the bioactivity of the particles and the morphology of the particles.

It would therefore be beneficial to provide a pharmaceutical powder batch having an average particle size on the order of 2 $\mu$m, a narrow particle size distribution and a low tendency to agglomerate. It would also be advantageous if the particles had a substantially spherical morphology. It would also be advantageous if such powders could be produced in a continuous, high-volume process.

SUMMARY OF THE INVENTION

The present invention is directed to improved pharmaceutical compositions in the form of fine dry powders and methods for producing such compositions. The present invention is also directed to devices incorporating such dry powders.

BRIEF DESCRIPTION OF THE DRAWINGS

FIG. 1 is a process block diagram showing one embodiment of the process of the present invention.

FIG. 36 is a block diagram of one embodiment of the present invention including a particle modifier.

DETAILED DESCRIPTION OF THE INVENTION

Figure 2:
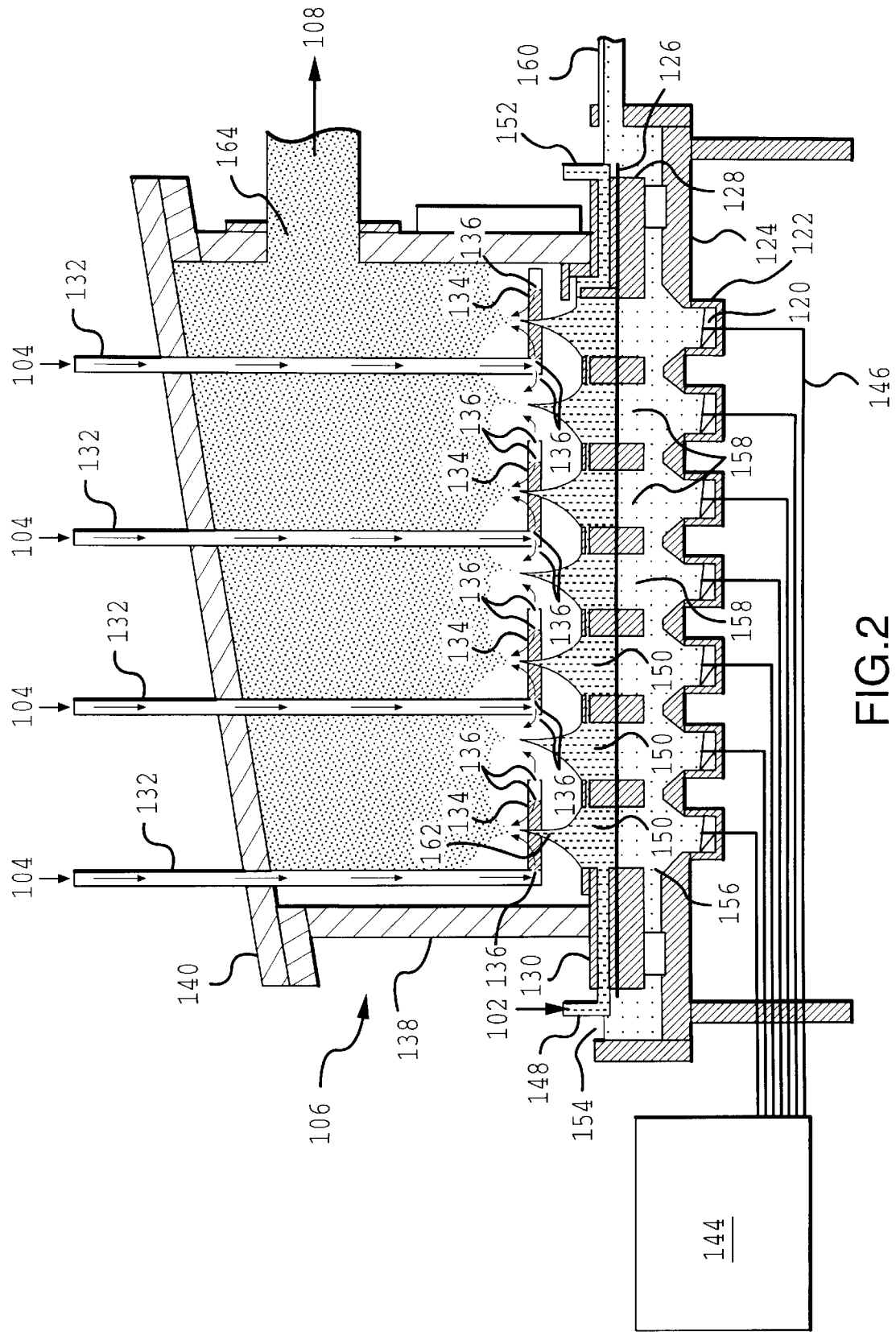
FIG. 2 is a side view in cross section of one embodiment of aerosol generator of the present invention.

An apparatus and accompanying method useful according to the present invention is described herein. Referring to FIG. 1, one embodiment of the process of the present invention is described. A liquid feed 102 and a carrier gas 104 are fed to an aerosol generator 106 where an aerosol 108 is produced. The aerosol 108 is then fed to a furnace 110 where liquid in the aerosol 108 is removed to produce particles 112 that are dispersed in and suspended by gas exiting the furnace 110. The particles 112 are then collected in a particle collector 114 to produce a particulate product 116.

As used herein, the liquid feed 102 is a feed that includes one or more flowable liquids as the major constituent(s), so that the feed is flowable. The liquid feed 102 need not comprise only liquid constituents. The liquid feed 102 may comprise only liquid phase constituents, or it may also include particulate material suspended in a liquid phase. The liquid feed 102 must, however, be capable of being atomized to form droplets of sufficiently small size for preparation of the aerosol 108. Therefore, if the liquid feed 102 includes suspended particles, those particles should be micro-sized or nano-sized. Such suspended particles should typically be smaller than about 1 micron in size, preferably smaller than about 0.5 micron in size, and more preferably smaller than about 0.3 micron in size.

The liquid feed 102 includes at least one precursor material for preparation of the particles 112. The precursor material may be a substance in either a liquid or solid phase of the liquid feed 102. The precursor material may undergo one or more chemical reactions in the furnace 110 to assist in production of the particles 112. Alternatively, the precursor material may contribute to formation of the particles 112 without undergoing chemical reaction. This could be the case, for example, when the liquid feed 102 includes, as a precursor material, suspended particles. The liquid feed 102 may include multiple precursor materials, which may be present together in a single phase or separately in multiple phases. For example, the liquid feed 102 may include multiple precursors in solution in a single liquid vehicle. Alternatively, one precursor material could be in a solid particulate phase and a second precursor material could be in a liquid phase. Also, one precursor material could be in one liquid phase and a second precursor material could be in a second liquid phase, such as could be the case for when the liquid feed 102 comprises an emulsion.

The carrier gas 104 may comprise any gaseous medium in which droplets produced from the liquid feed 102 may be dispersed in aerosol form. Also, the carrier gas 104 may be inert, in that the carrier gas 104 does not participate in formation of the particles 112. Alternatively, the carrier gas may have one or more active component(s) that contribute to formation of the particles 112. In that regard, the carrier gas may include one or more reactive components that react in the furnace 110 to contribute to formation of the particles 112. In many applications, air will be a satisfactory carrier gas, particularly when the particles 112 comprise oxide materials. In other instances, a relatively inert gas such as nitrogen may be required. This would sometimes be the case, for example, when preparing particles comprising sulfide materials or other materials that are free of oxygen.

The aerosol generator 106 must be capable of atomizing the liquid feed 102 to form droplets in a manner to permit the carrier gas 104 to sweep the droplets away to form the aerosol 108. The droplets comprise liquid from the liquid feed 102. The droplets may, however, also include nonliquid material, such as one or more small particles held in the droplet by the liquid. For example, when the particles 112 are composite particles, one phase of the composite may be provided in the liquid feed 102 in the form of suspended precursor particles and a second phase of the composite may be produced in the furnace 110 from one or more precursors in the liquid phase of the liquid feed 102. Furthermore the precursor particles could be included in the liquid feed 102, and therefore also in droplets of the aerosol 108, for the purpose only of dispersing the particles for subsequent compositional or structural modification during or after processing in the furnace 110 to remove liquid from the droplets.

The aerosol generator 106 is capable of producing the aerosol 108 such that it includes droplets having a weight average size of smaller than about 20 microns, preferably smaller than about 10 microns, more preferably from about 1 micron to about 5 microns, and most preferably about 3 microns. The aerosol generator is also capable of producing the aerosol 108 such that it includes only droplets of a narrow size distribution. Preferably, the droplets in the aerosol are such that at least 70 percent (more preferably at least 80 weight percent and most preferably at least 85 weight percent) of the droplets are smaller than about 20 microns, more preferably at least 70 weight percent (more preferably at least 80 weight percent and most preferably at least 85 weight percent) are smaller than about 10 microns, and even more preferably at least 70 weight percent (more preferably at least 80 weight percent and most preferably at least 85 weight percent) are smaller than about 5 microns. Most preferably, at least 70 weight percent (more preferably at least 80 weight percent and most preferably at least 90 weight percent) of the droplets are of a size of from about 1 micron to about 5 microns.

The aerosol generator 106 is also capable of producing the aerosol 108 such that it has a high loading, or high concentration, of the liquid feed 102 in droplet form. In that regard, the aerosol 108 preferably includes greater than about $5 \times 10^6$ droplets per cubic centimeter of the aerosol 108, more preferably greater than about $1 \times 10^7$ droplets per cubic centimeter of the aerosol 108 and most preferably greater than about $5 \times 10^7$ droplets per cubic centimeter of the aerosol 108. That the aerosol generator 106 can produce such a heavily loaded aerosol 108 is particularly surprising considering the high quality of the aerosol 108 with respect to small droplet size and narrow droplet size distribution. When the aerosol 108 includes droplets of an average size of about 3 microns, for example, droplet loading in the aerosol is such that the volumetric ratio of liquid feed 102 to carrier gas 104 in the aerosol 108 is typically larger than about 0.083 milliliters of liquid feed 102 per liter of carrier gas 102 in the aerosol 108, preferably larger than about 0.167 milliliters of liquid feed 102 per liter of carrier gas 104, and most preferably larger than about 0.333 milliliters of liquid feed 102 per liter of carrier gas 104. Stated another way, when average droplets in the aerosol 108 are about 3 microns in size, droplet loading in the aerosol 108 is such that the ratio of the rate of liquid feed 102 consumed in generating the aerosol 108 to the rate of carrier gas 104 consumed to generate the aerosol 108 is larger than about 5 milliliters per hour of liquid feed 102 per liter per minute of carrier gas 104, more preferably larger than about 10 milliliters per hour of liquid feed 102 per liter per minute of carrier gas 104, and most preferably larger than about 20 milliliters per hour of liquid feed 102 per liter per minute of carrier gas 104. This capability of the aerosol generator 106 to produce a heavily loaded aerosol 108 is even more surprising given the high droplet output rate of which the aerosol generator 106 is capable, as discussed more fully below. It will be appreciated that the concentration of liquid feed 102 in the aerosol 108 will depend upon the specific components and attributes of the liquid feed 102 and the size of the droplets produced in the aerosol 108. When reference is made to liters of carrier gas 104, it refers to the volume that the carrier gas 104 would occupy under conditions of standard transportation and pressure.

The furnace 110 may be any suitable device for heating the aerosol 108 to evaporate liquid from the droplets of the aerosol 108 and thereby permit formation of the particles 112. Typically, the furnace will be a tube furnace, so that the aerosol 108 moving into and through the furnace does not encounter sharp edges on which droplets could collect. Loss of droplets to collection at sharp surfaces results in lower yield of particles 112. More important, however, the accumulation of liquid at sharp edges can result in re-release of undesirably large droplets back into the aerosol 108, which can cause contamination of the particulate product 116 with undesirably large particles. Also, over time, such liquid collection at sharp surfaces can cause fouling of process equipment.

The particle collector 114, may be any suitable apparatus for collecting particles 112 to produce the particulate product 116. One preferred particle collector is a bag filter.

The process and apparatus of the present invention is well-suited for producing commercial-size batches of high quality particles of specialty materials. In that regard, the process and the accompanying apparatus provide versatility for preparing a wide variety of materials, and easily accommodate shifting of production between batches of different materials.

Figure 3:
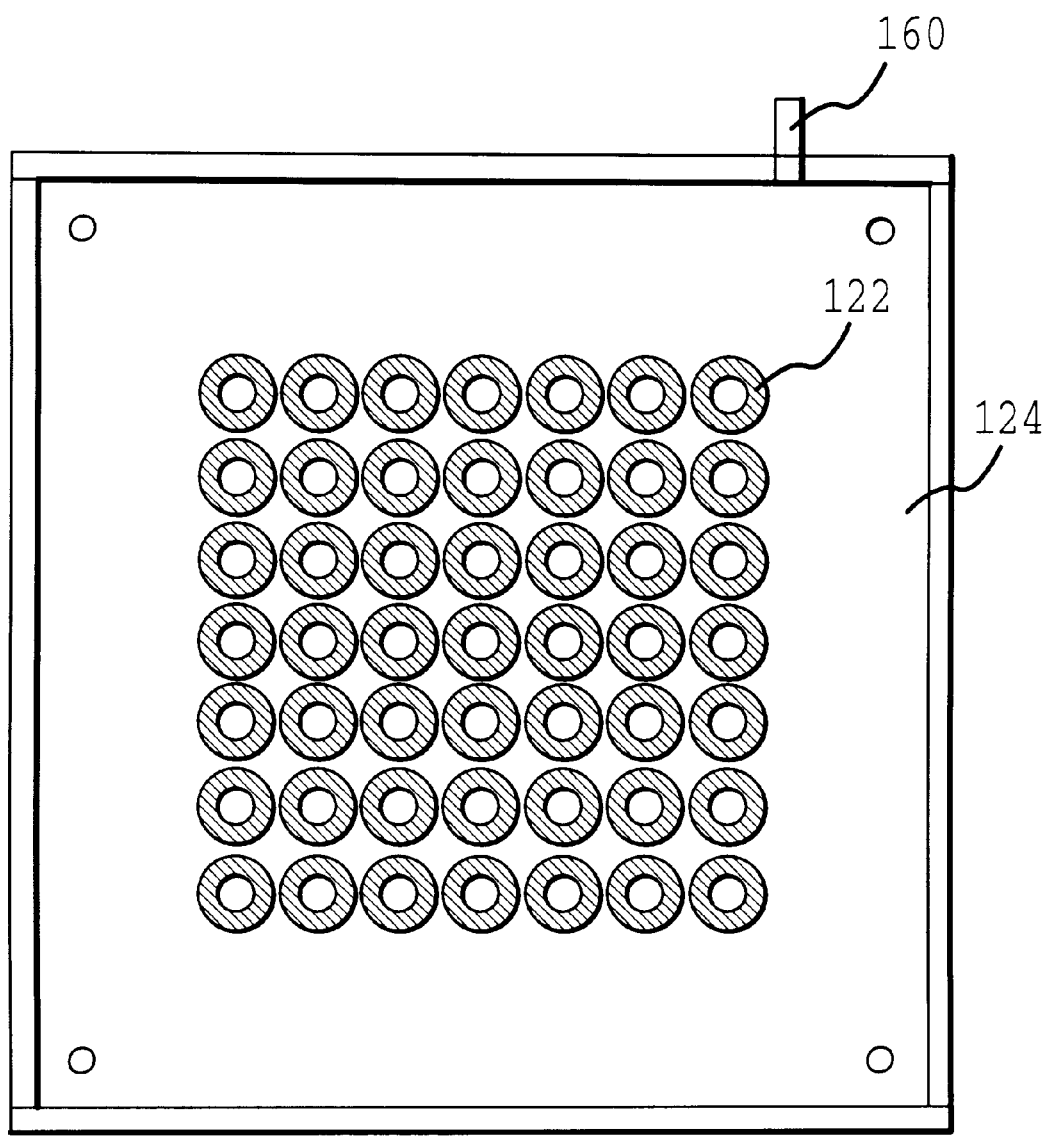
FIG. 3 is a top view of a transducer mounting plate showing the transducer array for use in an aerosol generator of the present invention.

Of significant importance to the operation of the process of the present invention is the aerosol generator 106, which must be capable of producing a high quality aerosol with high droplet loading, as previously noted. With reference to FIG. 2, one embodiment of an aerosol generator 106 of the present invention is described. The aerosol generator 106 includes a plurality of ultrasonic transducer discs 120 that are each mounted in a transducer housing 122. The transducer housings 122 are mounted to a transducer mounting plate 124, creating an array of the ultrasonic transducer discs 120. The aerosol generator 106, as shown in FIG. 2, includes forty-nine transducers in a 7×7 array. The array configuration is as shown in FIG. 3, which depicts the locations of the transducer housings 122 mounted to the transducer mounting plate 124.

With continued reference to FIG. 2, a separation membrane 126, in spaced relation to the transducer discs 120, is retained between a bottom retaining plate 128 and a top retaining plate 130. Gas delivery tubes 132 are connected to gas distribution manifolds 134, which have gas delivery ports 136. The gas distribution manifolds 134 are housed within a generator body 138 that is covered by generator lid 140. A transducer driver 144, having circuiting for driving the transducer discs 120, is electronically connected with the transducer discs 120 via electrical cables 146.

During operation of the aerosol generator 106, as shown in FIG. 2, the transducer discs 120 are activated by the transducer driver 144 via the electrical cables 146. Liquid feed 102 enters through a feed inlet 148 and flows through flow channels 150 to exit through feed outlet 152. An ultrasonically transmissive fluid, typically water, enters through a water inlet 154 to fill a water bath volume 156 and flow through flow channels 158 to exit through a water outlet 160. A proper flow rate of the ultrasonically transmissive fluid is necessary to prevent overheating of the ultrasonically transmissive fluid. Ultrasonic signals from the transducer discs 120 are transmitted, via the ultrasonically transmissive fluid, across the water bath volume 156, and ultimately across the separation membrane 126 to the liquid feed 102 in flow channels 150. The ultrasonic signals from the ultrasonic transducer discs 120 cause atomization cones 162 to develop in the liquid feed 102 at locations corresponding with the transducer discs 120. Carrier gas 104 is introduced into the gas delivery tubes 132 and delivered to the vicinity of the atomization cones 162 via gas delivery ports 136. Carrier gas exits the gas delivery ports 136 in a direction so as to impinge on the atomization cones 162, thereby sweeping away atomized droplets of the liquid feed 102 that are being generated from the atomization cones 162 and creating the aerosol 108, which exits the aerosol generator 106 through an aerosol exit opening 164.

Efficient use of the carrier gas 104 is an important aspect of the aerosol generator 106 used with the process of the present invention. The embodiment of the aerosol generator 106 shown in FIG. 2 includes two gas exit ports per atomization cone, with the exiting carrier gas 104 being directed at the surface of the atomization cones 162, thereby efficiently distributing the carrier gas 104 to critical portions of the liquid feed 102 for effective and efficient sweeping away of droplets as they form about the atomization cones 162. The aerosol generator 106, therefore, permits generation of the aerosol 108 with heavy loading with droplets of the carrier liquid 102, unlike aerosol generator designs do not efficiently focus gas delivery to the locations of droplet formation.

Another important feature of the aerosol generator 106, as shown in FIG. 2, is the use of the separation membrane 126, which protects the transducers discs 120 from direct contact with the liquid feed 102, which is often highly corrosive. Although the aerosol generator 106 could be made without the separation membrane 126, in which case the liquid feed 102 would be in direct contact with the transducer discs 120, the highly corrosive nature of the liquid feed 102 can often cause premature failure of the transducer discs 120. The use of the separation membrane 126, in combination with use of the ultrasonically transmissive fluid in the water bath volume 56 to provide ultrasonic coupling, significantly extends the life of the ultrasonic transducers 120. One disadvantage of using the separation membrane 126, however, is that the rate of droplet production from the atomization cones 162 is reduced, often by a factor of two or more, relative to designs in which the liquid feed 102 is in direct contact with the ultrasonic transducer discs 102. Even with the separation membrane 126, however, the aerosol generator 106 used with the present invention is capable of producing a high quality aerosol with heavy droplet loading, as previously discussed. Suitable materials for the separation membrane 126 include, for example, polyamides (such as Capton™ membranes from DuPont) and other polymer materials, glass, and plexiglass. The main requirements for the separation membrane 126 are corrosion resistance and impermeability.

One alternative to using the separation membrane 126 is to bind a corrosion-resistant coating onto the surface of the ultrasonic transducer discs 120, thereby preventing the liquid feed 102 from contacting the surface of the ultrasonic transducer discs 120. Examples of such coating materials include platinum, Teflon, epoxies and various plastics. Although the coating does typically extend transducer life, after extended operation the coatings sometimes separate from the transducer surface, impairing transducer operation.

The design for the aerosol generator 106 based on an array of ultrasonic transducers is versatile and is easily modified to accommodate different generator sizes for different applications. FIGS. 4–15 show component designs for an aerosol generator 106 including an array of 400 transducers.

Figure 4:
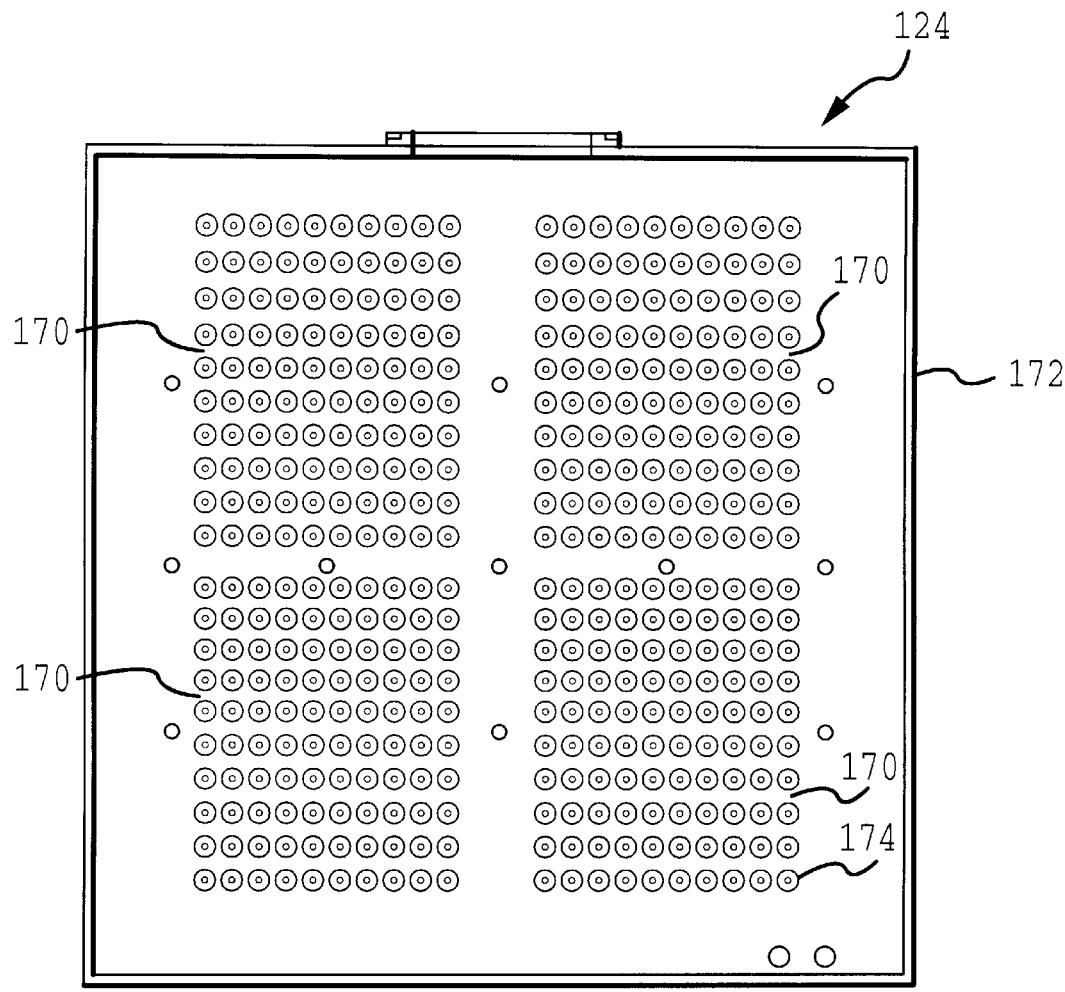
FIG. 4 is a top view of a transducer mounting plate for use in an ultrasonic generator of the present invention.
Figure 5:
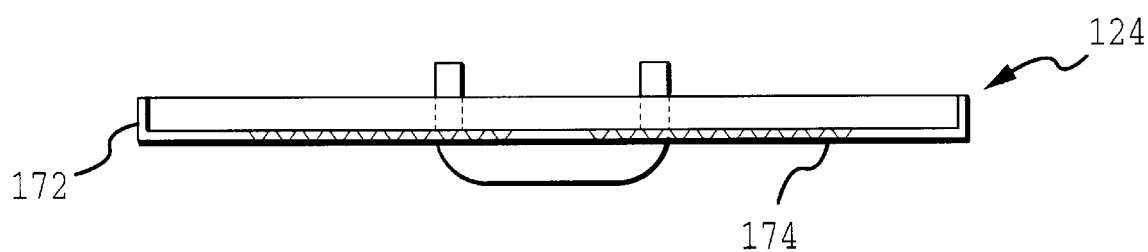
FIG. 5 is a side view of the transducer mounting plate shown in FIG. 4.

Referring first to FIGS. 4 and 5, the transducer mounting plate 124 is shown with a design to accommodate an array of 400 ultrasonic transducers, arranged in four subarrays of 100 ultrasonic transducers each. The transducer mounting plate 124 has integral vertical walls 172 for containing the ultrasonically transmissive fluid, typically water, in a water bath similar to the water bath volume 156 described previously with reference to FIG. 2.

Figure 6:
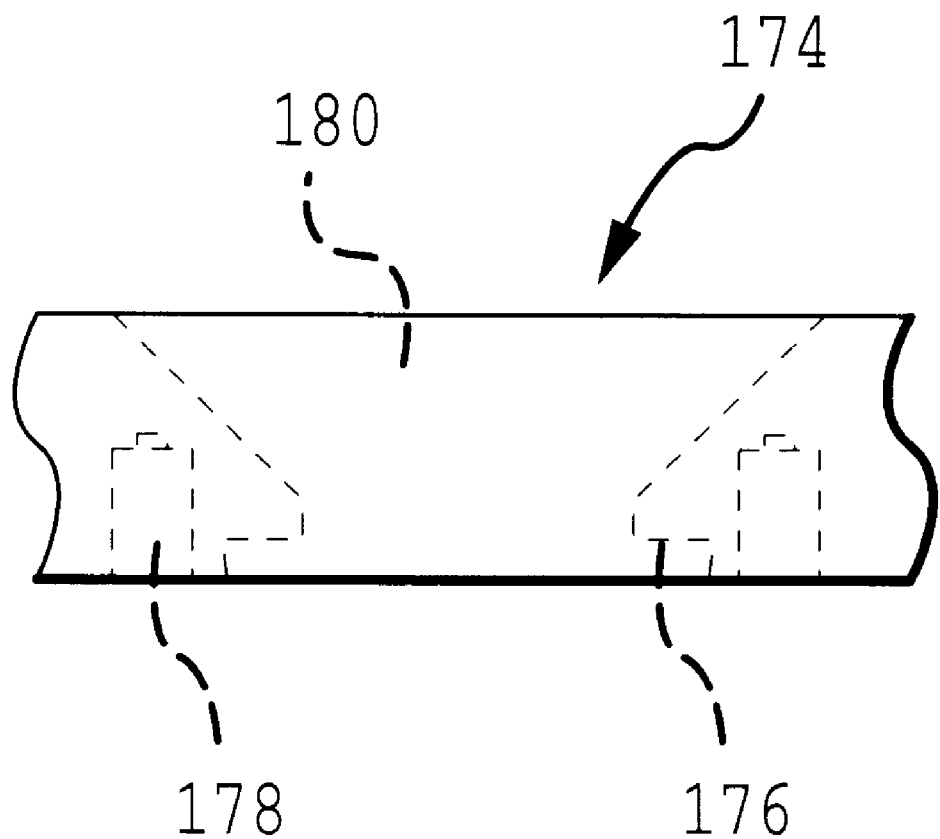
FIG. 6 is a side view showing the profile of a single transducer mounting receptacle of the transducer mounting plate shown in FIG. 4.

As shown in FIGS. 4 and 5, four hundred transducer mounting receptacles 174 are provided in the transducer mounting plate 124 for mounting ultrasonic transducers for the desired array. With reference to FIG. 6, the profile of an individual transducer mounting receptacle 174 is shown. A mounting seat 176 accepts an ultrasonic transducer for mounting, with a mounted ultrasonic transducer being held in place via screw holes 178. Opposite the mounting receptacle 176 is a flared opening 180 through which an ultrasonic signal may be transmitted for the purpose of generating the aerosol 108, as previously described with reference to FIG. 2. With the mounting seats 176, it is not necessary to use the separate transducer housings 122 that were previously described with reference to the embodiment of the aerosol generator 106 shown in FIG. 2.

Figure 7:
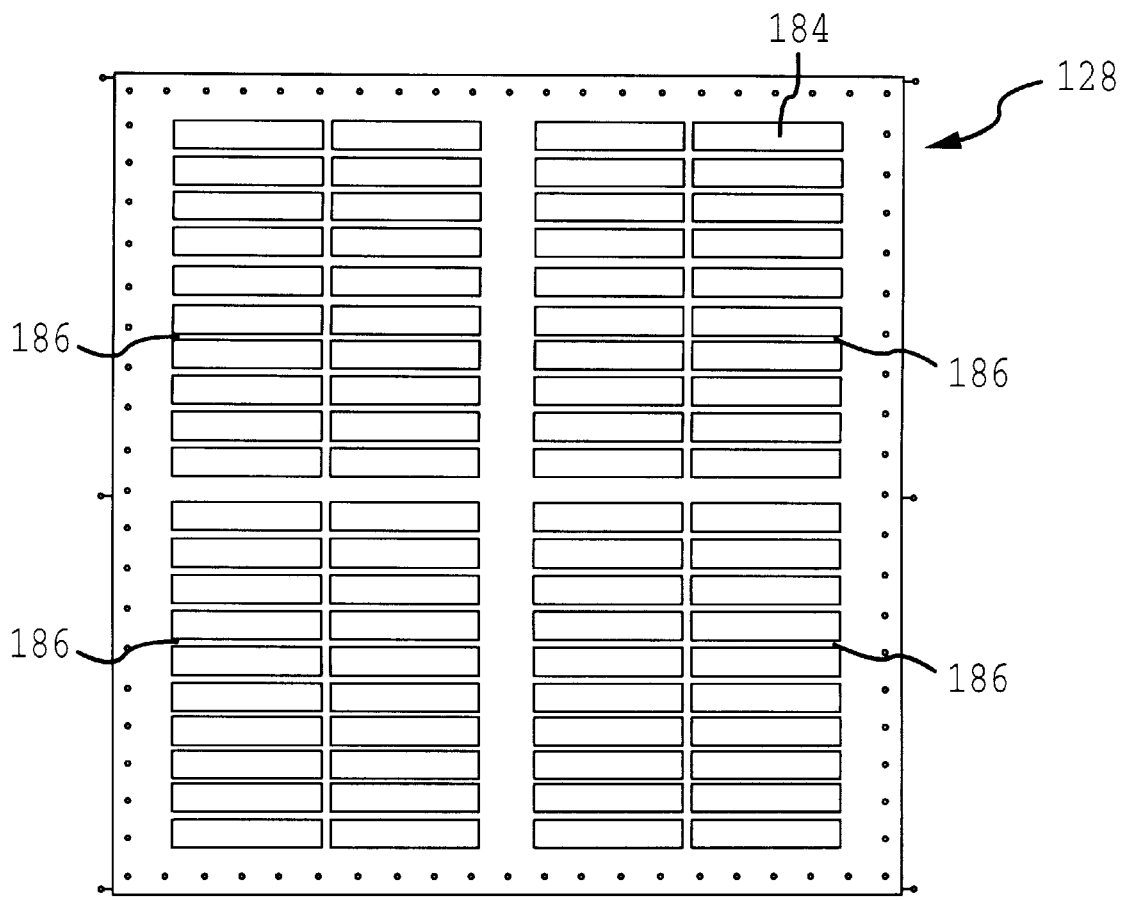
FIG. 7 is a top view of a bottom retaining plate for retaining a separation membrane for use in an aerosol generator of the present invention.

Referring now to FIG. 7, the bottom retaining plate 128 for a 400 transducer array is shown having a design for mating with the transducer mounting plate 124 (shown in FIGS. 4–5). The bottom retaining plate 128 has eighty openings 184, arranged in four subgroups 186 of twenty openings 184 each. Each of the openings 184 corresponds with five of the transducer mounting receptacles 174 (shown in FIGS. 4 and 5), when the bottom retaining plate 128 is mated with the transducer mounting plate 124 to create a volume for a water bath between the transducer mounting plate 124 and the bottom retaining plate 128. The openings 184, therefore, provide a pathway for ultrasonic signals generated by transducers to be transmitted through the bottom retaining plate.

Figure 8:
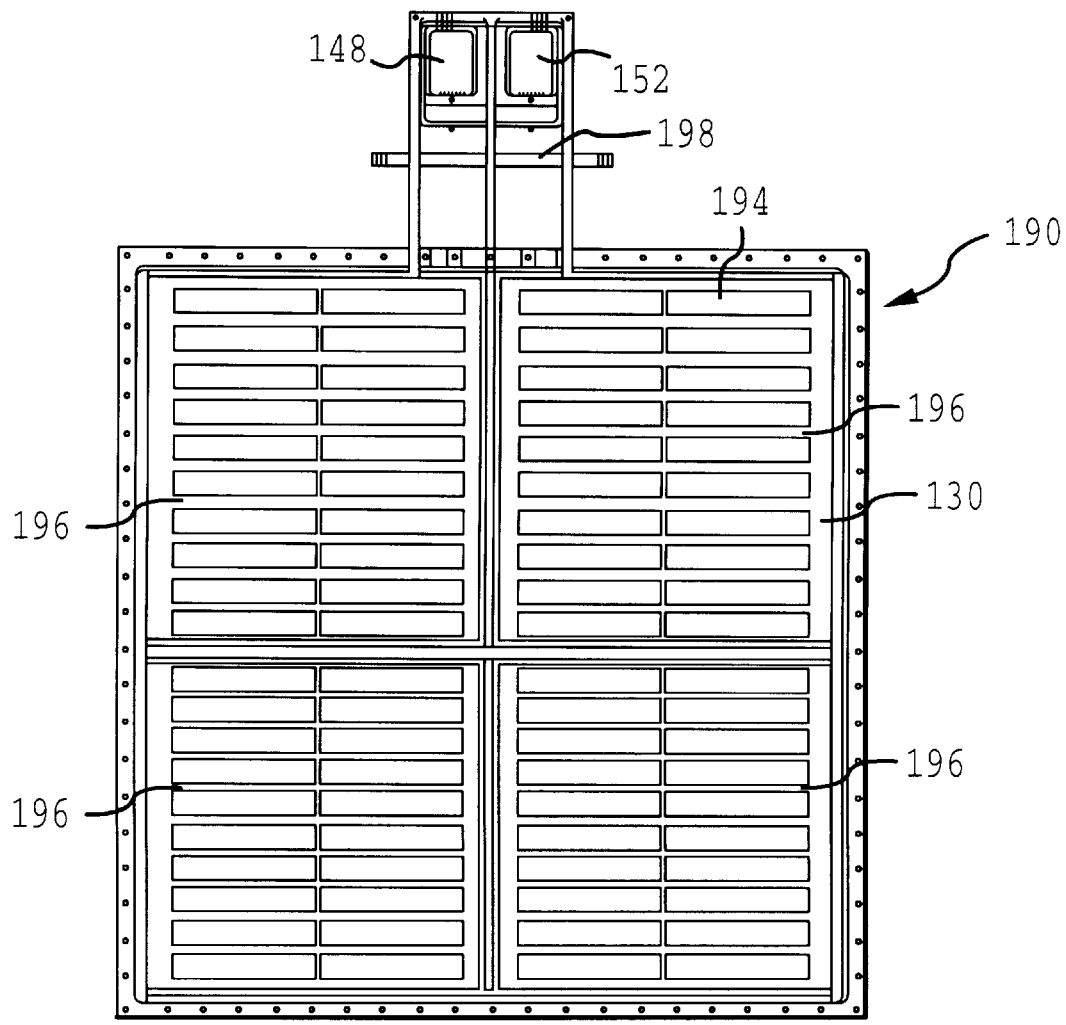
FIG. 8 is a top view of a liquid feed box having a bottom retaining plate to assist in retaining a separation membrane for use in an aerosol generator of the present invention.
Figure 9:
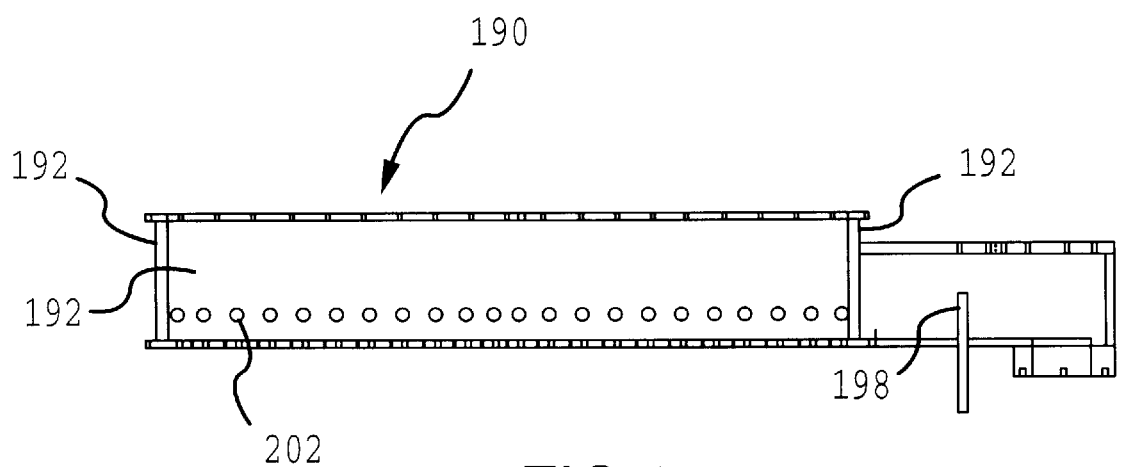
FIG. 9 is a side view of the liquid feed box shown in FIG. 8.

Referring now to FIGS. 8 and 9, a liquid feed box 190 for a 400 transducer array is shown having the top retaining plate 130 designed to fit over the bottom retaining plate 128 (shown in FIG. 7), with a membrane being retained between the bottom retaining plate 128 and the top retaining plate 130 when the aerosol generator 106 is assembled. The liquid feed box 190 also includes vertically extending walls 192 for containing liquid feed when the aerosol generator is in operation. Also shown in FIGS. 8 and 9 is the feed inlet 148 and the feed outlet 152. An adjustable weir 198 determines the level of liquid feed 102 in the liquid feed box 190 during operation of the aerosol generator 106.

The top retaining plate 130 of the liquid feed box 190 has eighty openings 194 therethrough, which are arranged in four subgroups 196 of twenty openings 194 each. The openings 194 of the top retaining plate 130 correspond in size with the openings 184 of the bottom retaining plate 128 (shown in FIG. 7). When the aerosol generator 106 is assembled, the openings 196 through the top retaining plate 130 and the openings 184 through the bottom retaining plate 128 are aligned, with a membrane positioned therebetween, to permit transmission of ultrasonic signals when the aerosol generator 106 is in operation.

Figure 10:
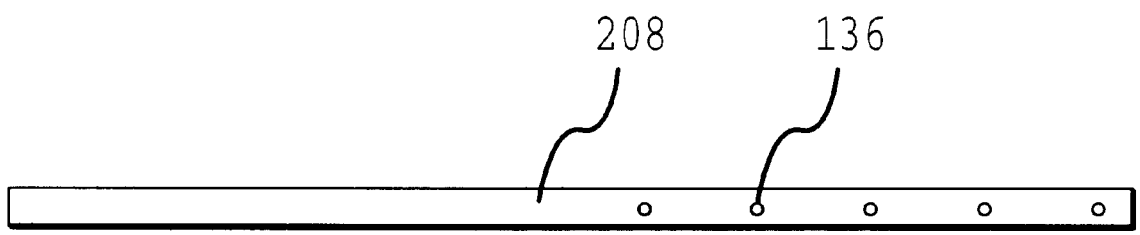
FIG. 10 is a side view of a gas tube for delivering gas within an aerosol generator of the present invention.

Referring now to FIGS. 8–10, a plurality of gas tube feed-through holes 202 extend through the vertically extended walls 192 to either side of the assembly including the feed inlet 148 and feed outlet 152 of the liquid feed box 190. The gas tube feed-through holes 202 are designed to permit insertion therethrough of gas tubes 208 of a design as shown in FIG. 10. When the aerosol generator 106 is assembled, a gas tube 208 is inserted through each of the gas tube feed-through holes 202 so that gas delivery ports 136 in the gas tube 208 will be properly positioned and aligned adjacent the openings 194 in the top retaining plate 130 for delivery of gas to atomization cones that develop in the liquid feed box 190 during operation of the aerosol generator 106.

Figure 11:
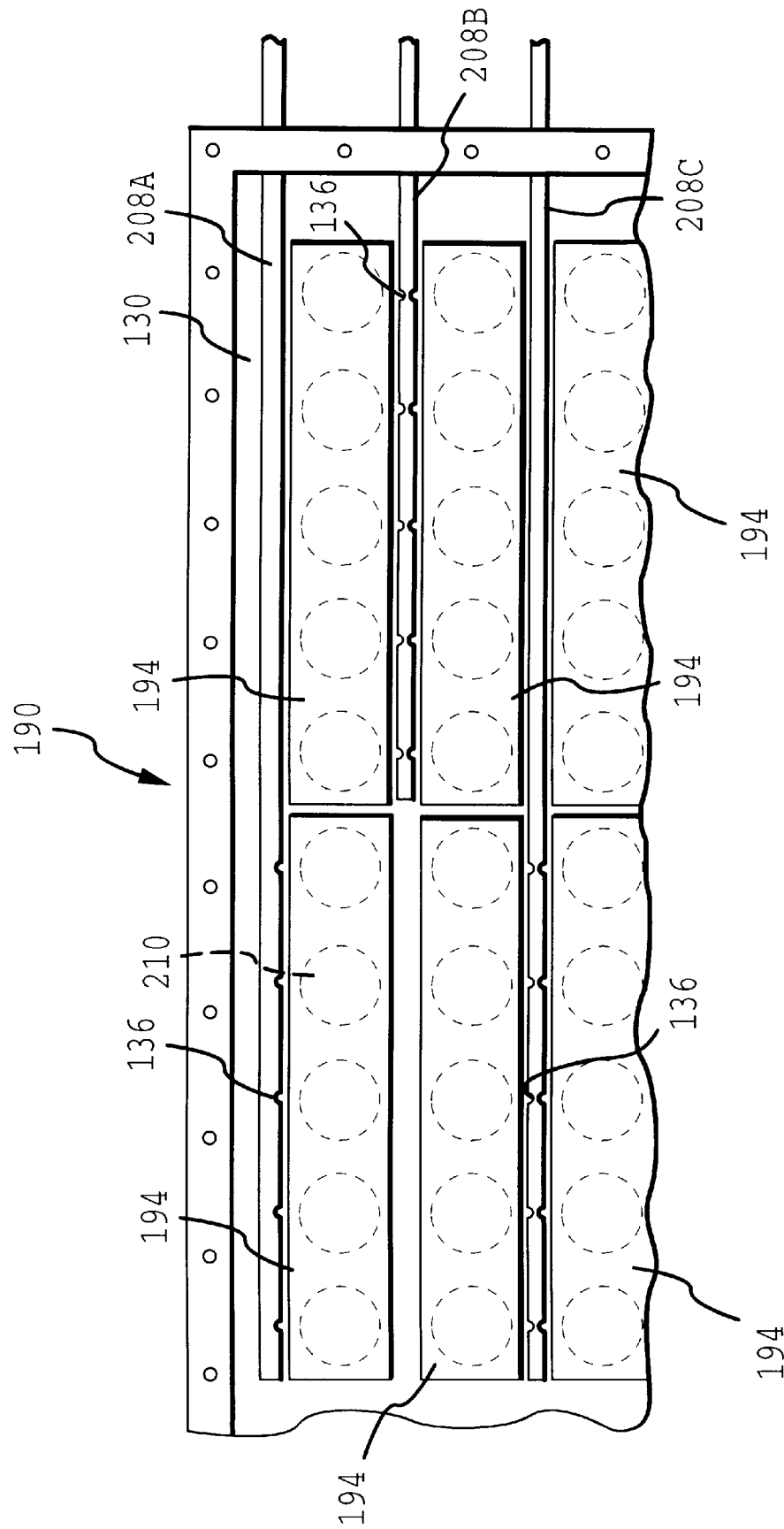
FIG. 11 shows a partial top view of gas tubes positioned in a liquid feed box for distributing gas relative to ultrasonic transducer positions for use in an aerosol generator of the present invention.

Referring now to FIG. 11 a partial view of the liquid feed box 190 is shown with gas tubes 208A, 208B and 208C positioned adjacent to the openings 194 through the top retaining plate 130. Also shown in FIG. 11 are the relative locations that ultrasonic transducers 210 occupy when the aerosol generator 106 is assembled. As seen in FIG. 11, the gas tube 208A, which is at the edge of the array, has five gas delivery ports 136. Each of the gas delivery ports 136 is positioned to deliver carrier gas 104 to a different one of atomization cones that develop over the ultrasonic transducers 210 when the aerosol generator 106 is operating. The gas tube 208B, which is one row in from the edge of the array, is a shorter tube that has ten gas delivery ports 136, five each on opposing sides of the gas tube 208B. The gas tube 208B, therefore, has gas delivery ports 136 for delivering gas to atomization cones corresponding with each of ten ultrasonic transducers 210. The third gas tube, 208C, is a longer tube that also has ten gas delivery ports 136 for delivering gas to atomization cones corresponding with ten ultrasonic transducers 210. The design shown in FIG. 11, therefore, includes one gas delivery port per ultrasonic transducer 210. Although this is a lower density of gas delivery ports 136 than the embodiment shown in FIG. 2, which includes two gas delivery ports per transducer, the design shown in FIG. 11 is, nevertheless, capable of producing a dense, high-quality aerosol without unnecessary waste of gas.

Figure 12:
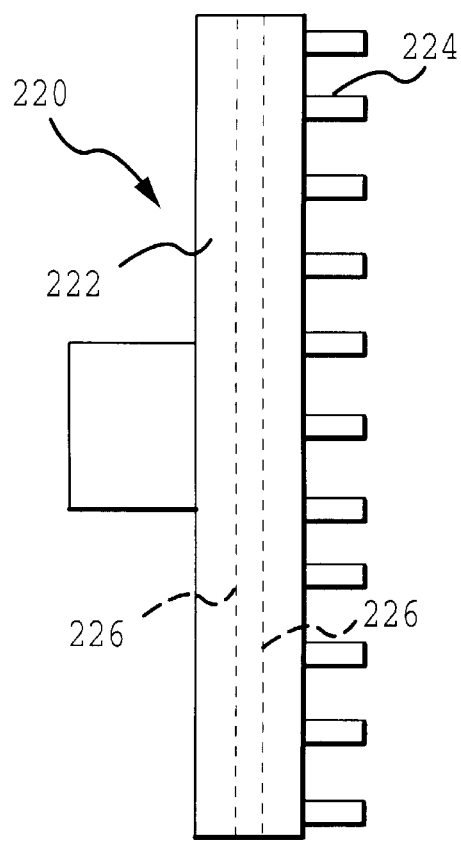
FIG. 12 is a top view of a gas manifold for distributing gas within an aerosol generator of the present invention.
Figure 13:
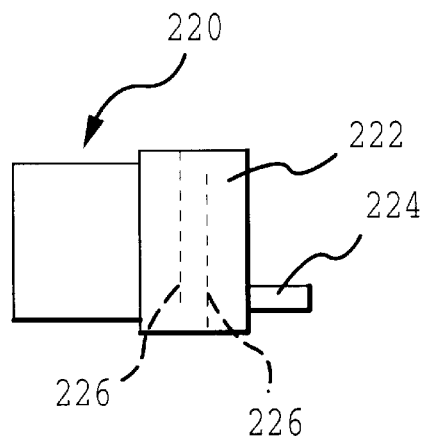
FIG. 13 is a side view of the gas manifold shown in FIG. 12.

Referring now to FIGS. 12 and 13, a gas manifold 220 is shown for distributing gas to the gas tubes 208 in a 400 transducer array design. The gas manifold 220 includes a gas distribution box 222, and piping stubs 224 for connection with gas tubes 208 (shown in FIG. 10). Inside the gas distribution box 222 are two gas distribution plates 226 that form a flow path to assist in distributing the gas equally throughout the gas distribution box 222, to promote substantially equal delivery of gas through the piping stubs 224. The gas manifold 220, as shown in FIGS. 12 and 13, is designed to feed eleven gas tubes 208. For the 400 transducer design, a total of four gas manifolds 220 are required.

Figure 14:
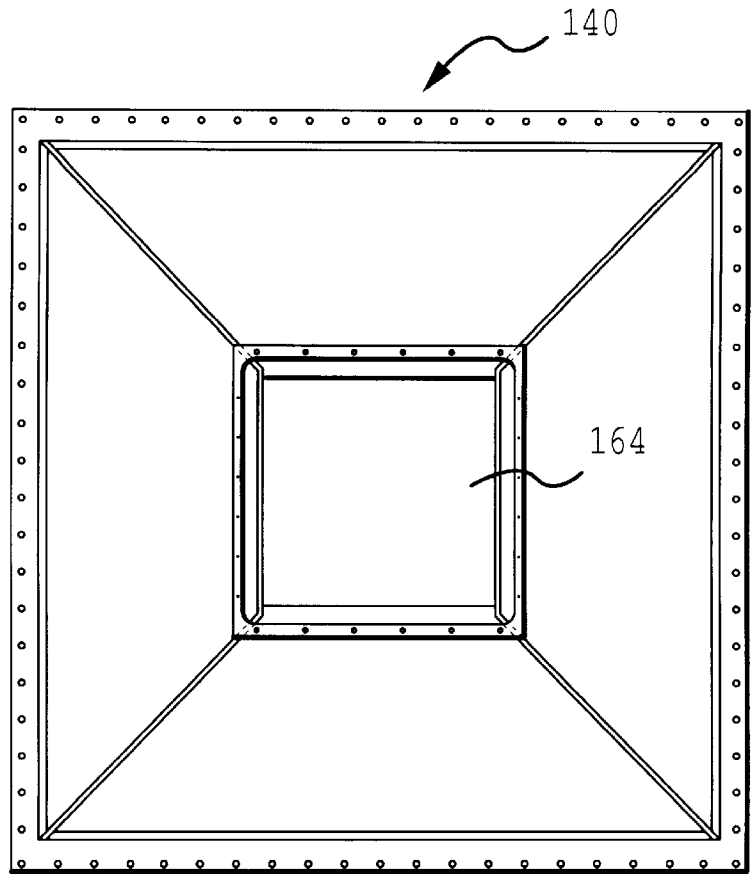
FIG. 14 is a top view of a generator lid of a hood design for use in an aerosol generator of the present invention.
Figure 15:
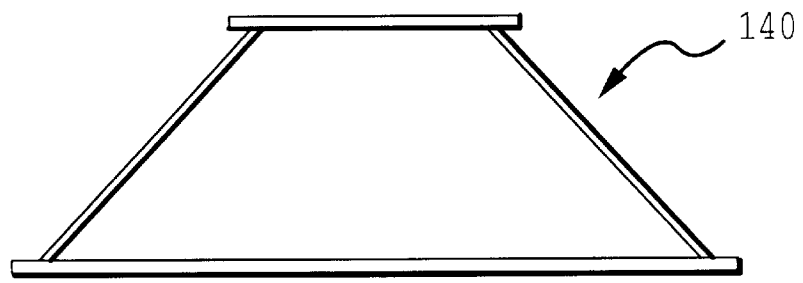
FIG. 15 is a side view of the generator lid shown in FIG. 14.

Referring now to FIGS. 14 and 15, the generator lid 140 is shown for a 400 transducer array design. The generator lid 140 mates with and covers the liquid feed box 190 (shown in FIGS. 8 and 9). The generator lid 140, as shown in FIGS. 14 and 15, has a hood design to permit easy collection of the aerosol 108 without subjecting droplets in the aerosol 108 to sharp edges on which droplets may coalesce and be lost, and possibly interfere with the proper operation of the aerosol generator 106. When the aerosol generator 106 is in operation, the aerosol 108 would be withdrawn via the aerosol exit opening 164 through the generator cover 140.

Figure 16:
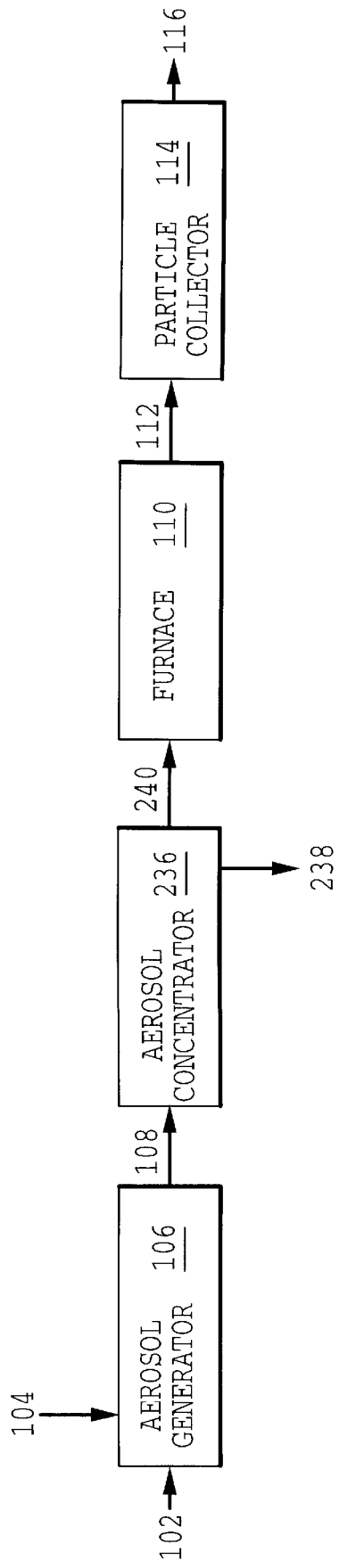
FIG. 16 is a process block diagram of one embodiment in the present invention including an aerosol concentrator.
Figure 17:
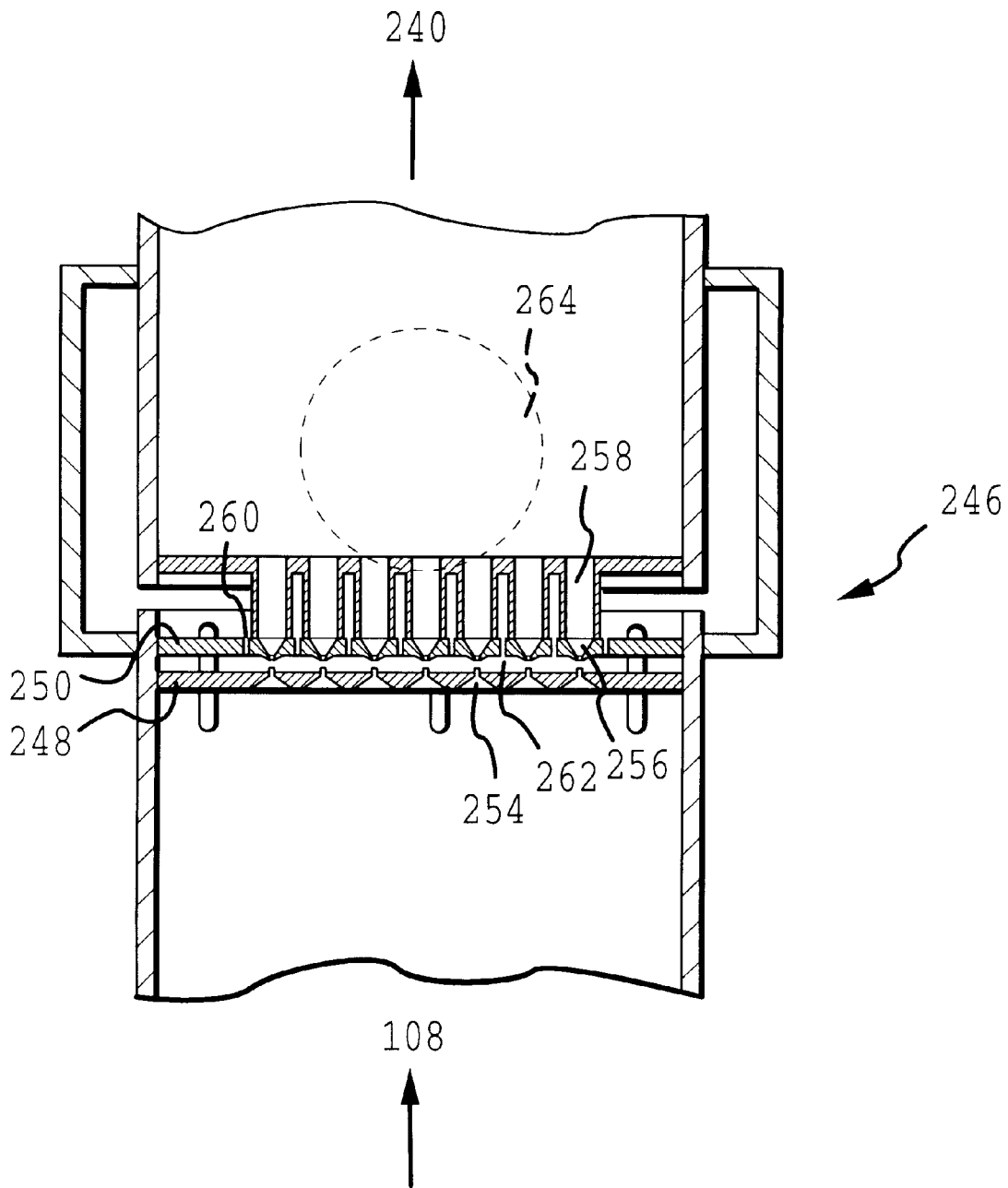
FIG. 17 is a top view in cross section of a virtual impactor that may be used for concentrating an aerosol according to the present invention.
Figure 18:
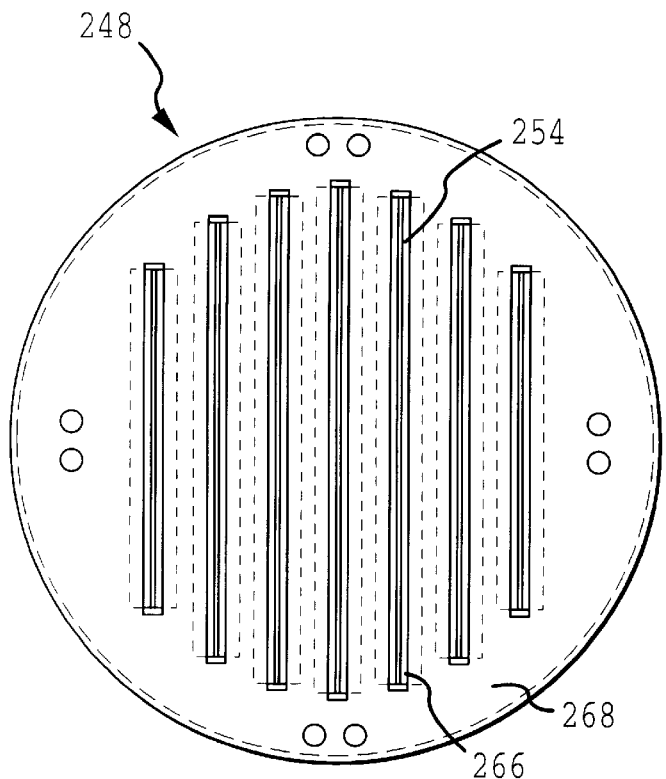
FIG. 18 is a front view of an upstream plate assembly of the virtual impactor shown in FIG. 17.
Figure 20:
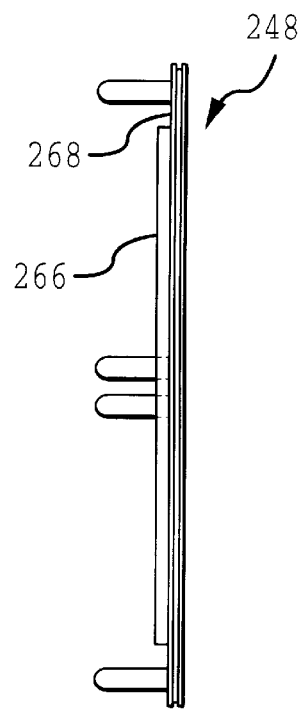
FIG. 20 is a side view of the upstream plate assembly shown in FIG. 18.
Figure 19:
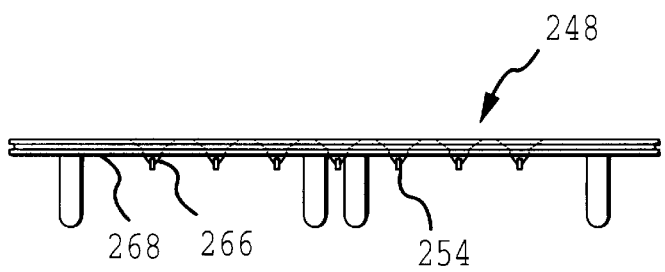
FIG. 19 is a top view of the upstream plate assembly shown in FIG. 18.
Figure 21:
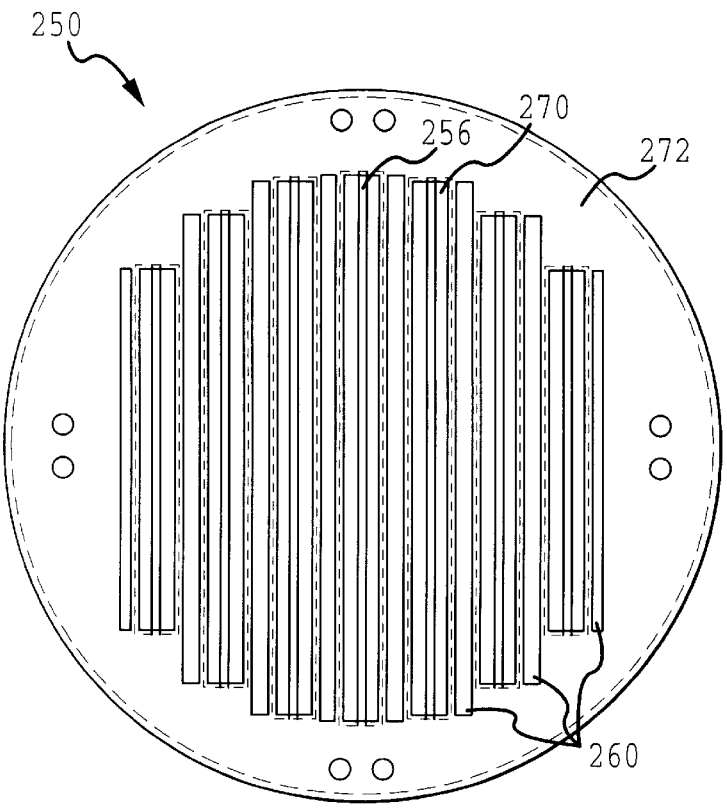
FIG. 21 is a front view of a downstream plate assembly of the virtual impactor shown in FIG. 17.
Figure 23:
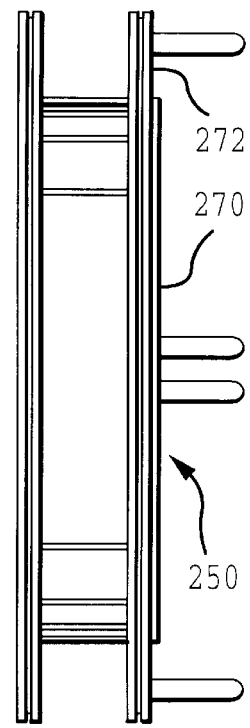
FIG. 23 is a side view of the downstream plate assembly shown in FIG. 21.
Figure 22:
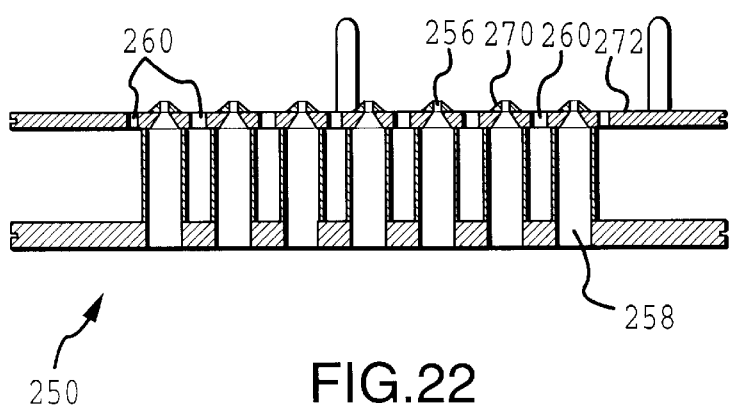
FIG. 22 is a top view of the downstream plate assembly shown in FIG. 21.

Although the aerosol generator 106 produces a high quality aerosol 108 having a high droplet loading, it is often desirable to further concentrate the aerosol 108 prior to introduction into the furnace 110. Referring now to FIG. 16, a process flow diagram is shown for an one embodiment of the present invention involving such concentration of the aerosol 108. As shown in FIG. 16, the aerosol 108 from the aerosol generator 106 is sent to an aerosol concentrator 236 where excess carrier gas 238 is withdrawn from the aerosol 108 to produce a concentrated aerosol 240, which is then fed to the furnace 110.

The aerosol concentrator 236 typically includes one or more virtual impactor capable of concentrating droplets in the aerosol 108 by a factor of greater than about 2, preferably by a factor of than about 5, and most preferably by a factor of greater than about 10, to produce the concentrated aerosol 240. According to the present invention, the concentrated aerosol 240 should typically contain greater than about $1 \times 10^7$ droplets per cubic centimeter, and more preferably from about $5 \times 10^7$ to about $5 \times 10^8$ droplets per cubic centimeter. A concentration of about $1 \times 10^8$ droplets per cubic centimeter of the concentrated aerosol is particularly preferred, because when the concentrated aerosol 240 is loaded more heavily than that, then the frequency of collisions between droplets becomes large enough to impair the properties of the concentrated aerosol 240, resulting in potential contamination of the particulate product 116 with an undesirably large quantity of over-sized particles. For example, if the aerosol 108 has a concentration of about $1 \times 10^7$ droplets per cubic centimeter, and the aerosol concentrator 236 concentrates droplets a factor of 10, then the concentrated aerosol 240 will have a concentration of about $1 \times 8$ droplets per cubic centimeter. Stated another way, for example, when the aerosol generator generates the aerosol 108 with average droplets of about three microns in size, the aerosol 108 with a droplet loading of about 0.167 milliliters liquid feed 102 per liter of carrier gas 104, the concentrated aerosol 240 would be loaded with about 1.67 milliliters of liquid feed 102 per liter of carrier gas 104. Stated as a ratio of the rate of liquid feed 102 in the aerosol 108 to the rate of carrier gas 104 in the aerosol 108, with an average droplet size of about three microns, and loading in the aerosol 108 of 10 milliliters per hour of liquid feed 102 per liter per minute of carrier gas 104, concentration by ten times would result in a concentrated aerosol 240 having a ratio of approximately 100 milliliters per hour of liquid feed 102 per liter per minute of carrier gas 104.

Having a high droplet loading in aerosol feed to the furnace provides the important advantage of reducing the heating demand on the furnace and the size of flow conduits required through the furnace. Concentration of the aerosol stream prior to entry into the furnace, therefore, provides a substantial advantage relative to processes that process leaner aerosol streams.

The excess carrier gas 238 that is removed in the aerosol concentrator 236 typically includes extremely small droplets that are also removed from the aerosol 108. For example, a virtual impactor sized to treat an aerosol stream having an average droplet size of about three microns might be designed to remove with the excess carrier gas 238 most droplets smaller than about 1 micron in size. Other designs are also possible. When using the aerosol generator 106 with the present invention, however, the loss of these very small droplets in the aerosol concentrator 236 will typically constitute no more than about ten percent by weight, and more preferably no more than about 5 percent by weight, of the droplets originally in the aerosol stream that is fed to the concentrator 236.

One embodiment of a virtual impactor that could be used as the aerosol concentrator 236 will now be described with reference to FIGS. 17–23. A virtual impactor 246 includes an upstream plate assembly 248 (details shown in FIGS. 18–20) and a downstream plate assembly 250 (details shown in FIGS. 21–23), with a concentrating chamber 262 located between the upstream plate assembly 248 and the downstream plate assembly 250.

Through the upstream plate assembly 248 are a plurality of vertically extending inlet slits 254. The downstream plate assembly 250 includes a plurality of vertically extending exit slits 256 that are in alignment with the inlet slits 254. The exit slits 254 are, however, slightly wider than the inlet slits 254. The downstream plate assembly 250 also includes flow channels 258 that extend substantially across the width of the entire downstream plate assembly 250, with each flow channel 258 being adjacent to an excess gas withdrawal port 260.

During operation, the aerosol 108 passes through the inlet slits 254 and into the concentrating chamber 262. Excess carrier gas 238 is withdrawn from the concentrating chamber 262 via the excess gas withdrawal ports 260. The withdrawn excess carrier gas 238 then exits via a gas duct port 264. That portion of the aerosol 108 that is not withdrawn through the excess gas withdrawal ports 260 passes through the exit slits 256 and the flow channels 258 to form the concentrated aerosol 240. Those droplets passing across the concentrating chamber 262 and through the exit slits 256 are those droplets of a large enough size to have sufficient momentum to resist being withdrawn with the excess carrier gas 238.

As seen best in FIGS. 18–23, the inlet slits 254 of the upstream plate assembly 248 include inlet nozzle extension portions 266 that extend outward from the plate surface 268 of the upstream plate assembly 248. The exit slits 256 of the downstream plate assembly 250 include exit nozzle extension portions 270 extending outward from a plate surface 272 of the downstream plate assembly 250. These nozzle extension portions 266 and 270 are important for operation of the virtual impactor 246, because having these nozzle extension portions 266 and 270 permits a very close spacing to be attained between the inlet slits 254 and the exit slits 256 across the concentrating chamber 262, while also providing a relatively large space in the concentrating chamber 262 to facilitate efficient removal of the excess carrier gas 238.

Also as best seen in FIGS. 18–23, the inlet slits 254 have widths that flare outward toward the side of the upstream plate assembly 248 that is first encountered by the aerosol 108 during operation. This flared configuration reduces the sharpness of surfaces encountered by the aerosol 108, reducing the loss of aerosol droplets and potential interference from liquid buildup that could occur if sharp surfaces were present. Likewise, the exit slits 256 have a width that flares outward towards the flow channels 258, thereby allowing the concentrated aerosol 240 to expand into the flow channels 258 without encountering sharp edges that could cause problems.

As noted previously, both the inlet slits 254 of the upstream plate assembly 248 and the exit slits 256 of the downstream plate assembly 250 are vertically extending. This configuration is advantageous for permitting liquid that may collect around the inlet slits 254 and the exit slits 256 to drain away. The inlet slits 254 and the exit slits 256 need not, however, have a perfectly vertical orientation. Rather, it is often desirable to slant the slits backward (sloping upward and away in the direction of flow) by about five to ten degrees relative to vertical, to enhance draining of liquid off of the upstream plate assembly 248 and the downstream plate assembly 250. This drainage function of the vertically extending configuration of the inlet slits 254 and the outlet slits 256 also inhibits liquid build-up in the vicinity of the inlet slits 248 and the exit slits 250, which liquid build-up could result in the release of undesirably large droplets into the concentrated aerosol 240.

As discussed previously, the aerosol generator 106 of the present invention produces a concentrated, high quality aerosol of micro-sized droplets having a relatively narrow size distribution. It has been found, however, that for many applications the process of the present invention is significantly enhanced by further classifying by site the droplets in the aerosol 108 prior to introduction of the droplets into the furnace 110. In this manner, the size and size distribution of particles in the particulate product 116 is further controlled.

Figure 24:
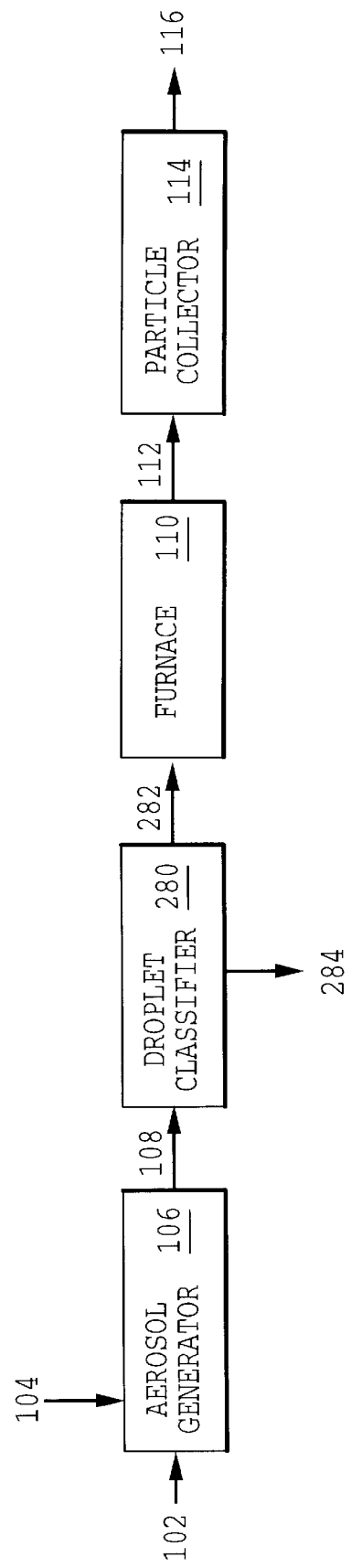
FIG. 24 is a process block diagram of one embodiment of the process of the present invention including a droplet classifier.

Referring now to FIG. 24, a process flow diagram is shown for one embodiment of the process of the present invention including such droplet classification. As shown in FIG. 24, the aerosol 108 from the aerosol generator 106 goes to a droplet classifier 280 where oversized droplets are removed from the aerosol 108 to prepare a classified aerosol 282. Liquid 284 from the oversized droplets that are being removed is drained from the droplet classifier 280. This drained liquid 284 may advantageously be recycled for use in preparing additional liquid feed 102.

Although any suitable droplet classifier may be used for removing droplets above a predetermined size, a preferred droplet classifier is an impactor. One embodiment of an impactor for use with the present invention will be described with referenced FIGS. 25–29.

Figure 25:
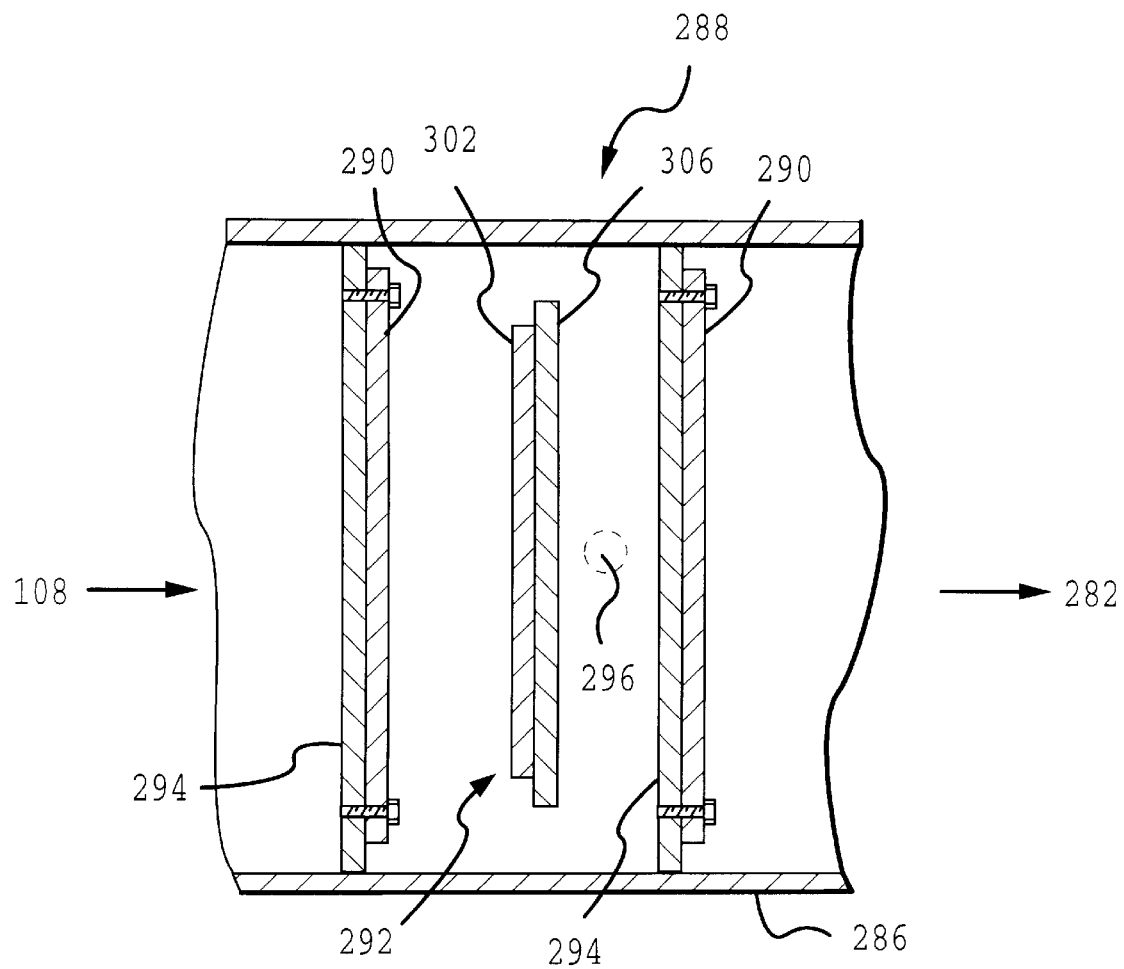
FIG. 25 is a top view in cross section of a virtual impactor of the present invention for use in classifying an aerosol.

As seen in FIG. 25, an impactor 288 has disposed in a flow conduit 286 two flow control plates 290, between which is located an impactor plate assembly 292. The flow control plates 290 are conveniently mounted on mounting plates 294. A drain 296 is located between the flow control plates 290.

Figure 26:
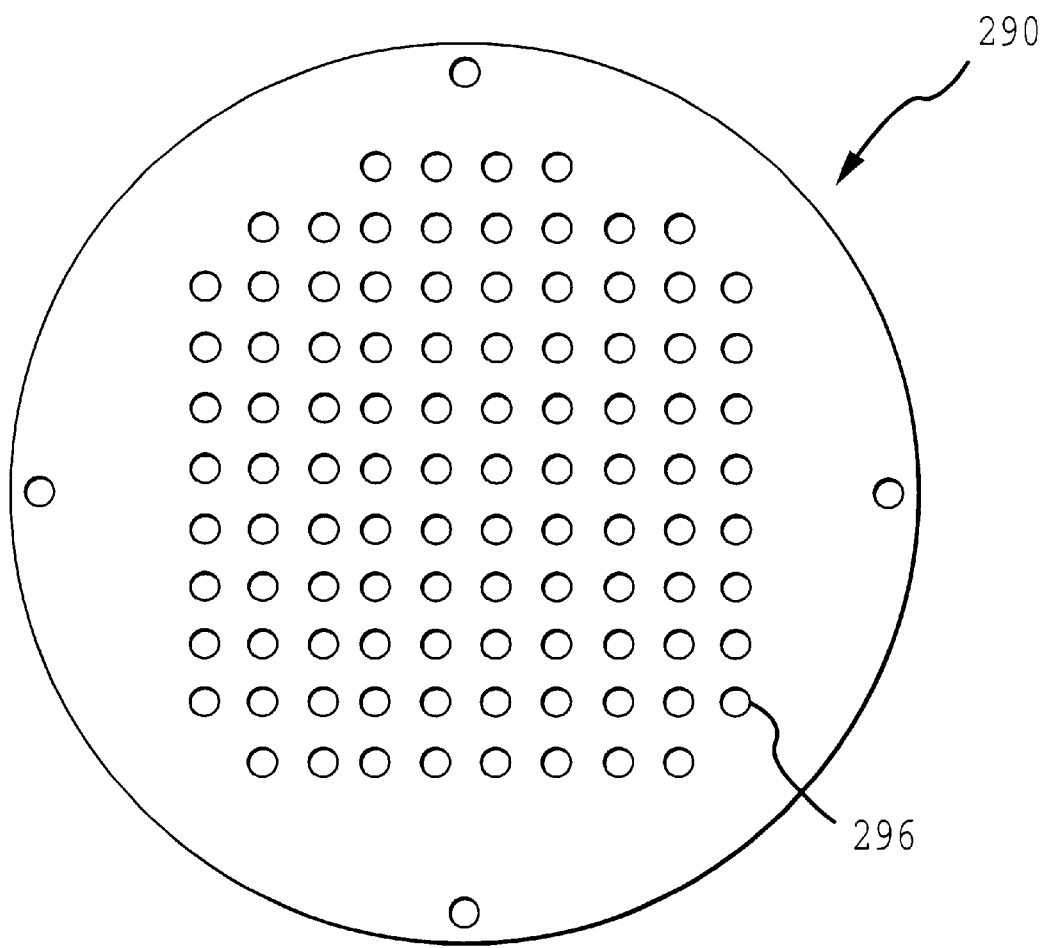
FIG. 26 is a front view of a flow control plate of the impactor shown in FIG. 25.

The flow control plates 290 are used to channel the flow of the aerosol stream toward and away from the impactor plate assembly 292 in a manner with controlled flow characteristics that are desirable for proper impaction of oversize droplets on the impactor plate assembly 292 for removal through the drain 296. One embodiment of the flow control plate 290 is shown in FIG. 26. The flow control plate 290 has an array of circular flow ports 296 for channeling flow of the aerosol 108 towards the impactor plate assembly 292 and for channeling flow of the classified aerosol 282 away from the impactor plate assembly 292.

Figure 27:
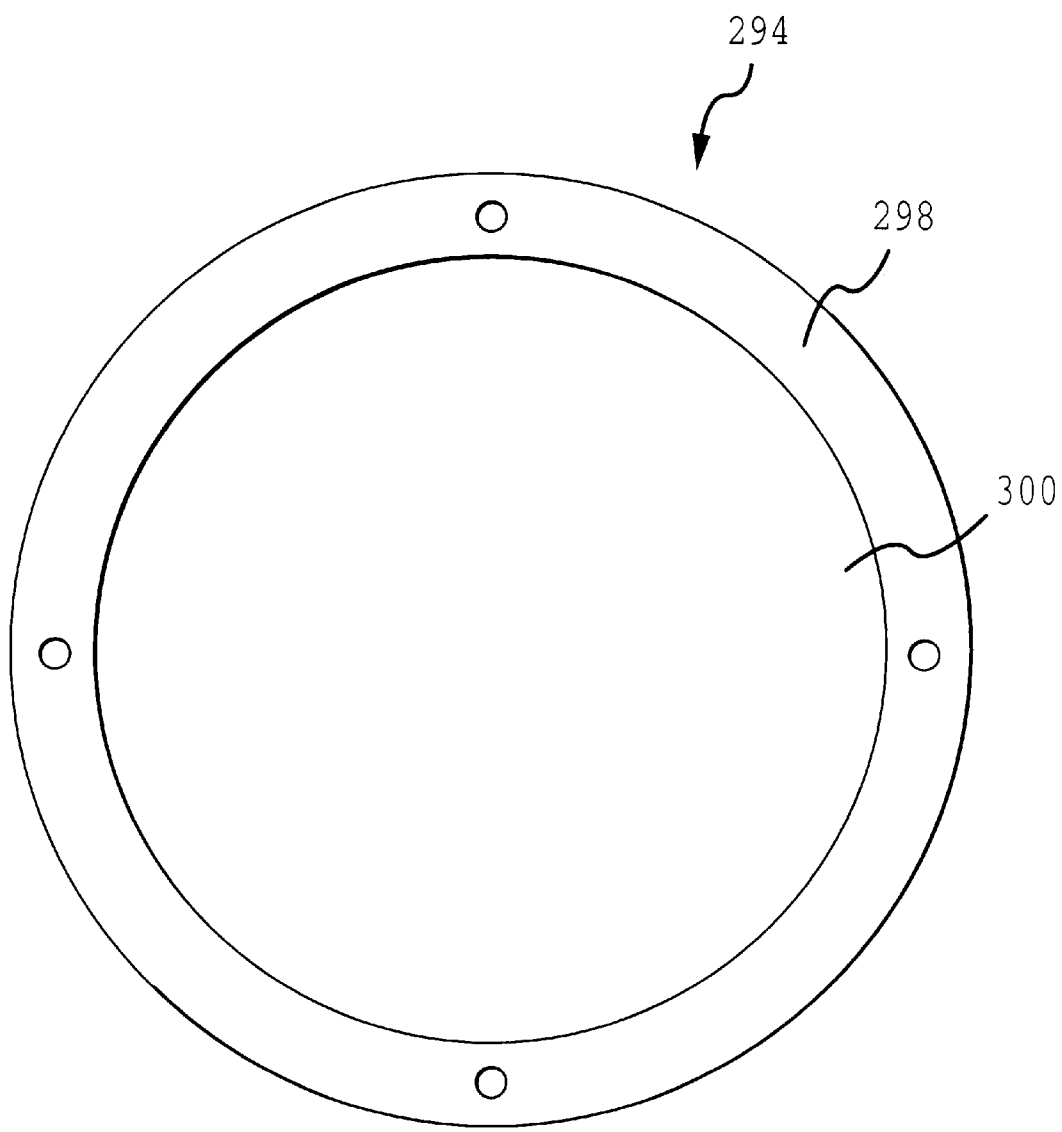
FIG. 27 is a front view of a mounting plate of the impactor shown in FIG. 25.

Details of the mounting plate 294 are shown in FIG. 27. The mounting plate 294 has a mounting flange 298 with a large diameter flow opening 300 passing therethrough to permit access of the aerosol 108 to the flow ports 296 of the flow control plate 290 (shown in FIG. 26).

Figure 28:
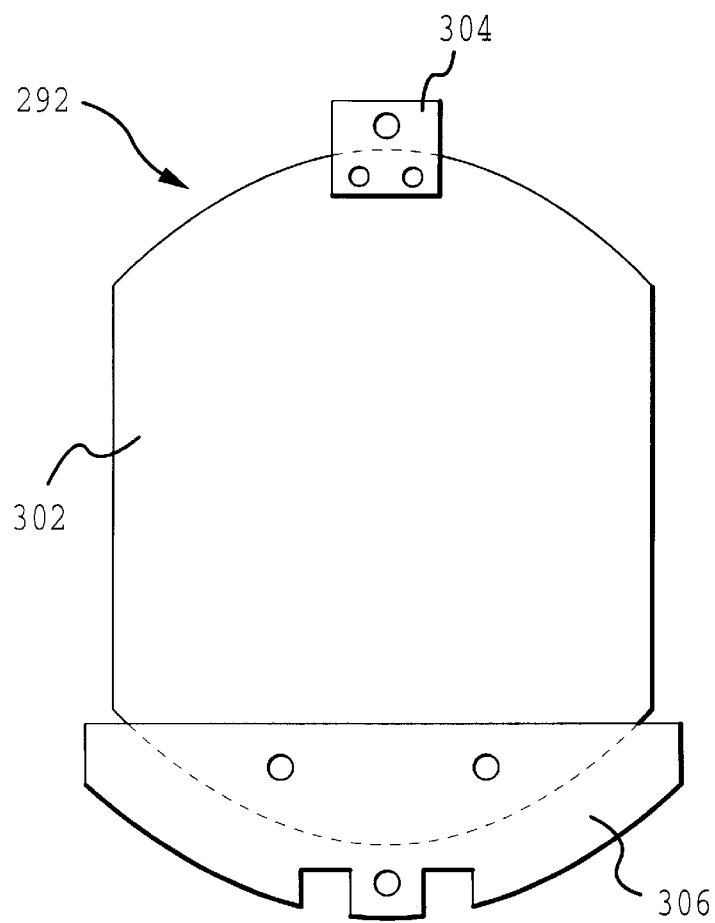
FIG. 28 is a front view of the impactor plate assembly of the impactor shown in FIG. 25.
Figure 29:
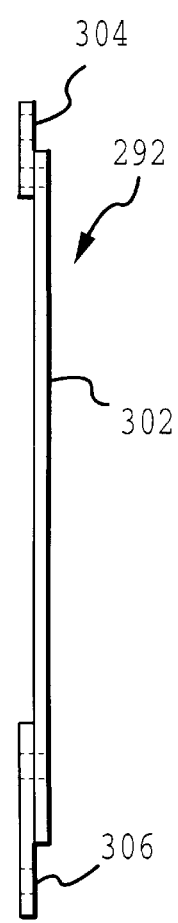
FIG. 29 is a side view of the impactor plate assembly shown in FIG. 28.

Referring now to FIGS. 28 and 29, one embodiment of an impactor plate assembly 292 is shown. The impactor plate assembly 292 includes an impactor plate 302 and mounting brackets 304 and 306 used to mount the impactor plate 302 inside of the flow conduit 286. The impactor plate 302 is sized and spaced a distance from the flow channel plates 290 so that droplets larger than a predetermined size will have a momentum that is too large for those particles to change flow direction to navigate around the impactor plate 302. Those large droplets will, therefore, impact on the impactor plate 302 and will drain down the impactor plate 302 to collect at the bottom of the conduit 286 and drain out of the drain 296.

During operation of the impactor 288, the aerosol 108 from the aerosol generator 106 passes through the upstream flow control plate 290. Most of the droplets in the aerosol navigate around the impactor plate 302 and exit the impactor 288 through the downstream flow control plate 290 in the classified aerosol 282. Droplets in the aerosol 108 that are too large to navigate around the impactor plate 302 will impact on the impactor plate 302 and drain through the drain 296 to be collected with the drained liquid 284 (as shown in FIG. 24).

The configuration of the impactor plate 302 shown in FIG. 28 represents only one of many possible configurations for the impactor plate 302. For example, the impactor 288 could include an upstream flow control plate 290 having vertically extending flow slits therethrough that are offset from vertically extending flow slits through the impactor plate 302, such that droplets too large to navigate the change in flow due to the offset of the flow splits between the flow control plate 290 and the impactor plate 302 would impact on the impactor plate 302 to be drained away. Other designs are also possible.

In a preferred embodiment of the present invention, the droplet classifier 280 is typically designed to remove droplets from the aerosol 108 that are larger than about 10 microns in size, more preferably to remove droplets of a size larger than about 8 microns in site and most preferably to remove droplets larger than about 5 microns in size. Depending upon the specific application, however, the droplet size for removal may be varied by changing the spacing between the flow control plate 290 and the impactor plate 302 and by varying the configuration of the impactor plate 302. Because the aerosol generator 106 of the present invention initially produces a high quality aerosol 108, having a relatively narrow size distribution of droplets, typically less than about 25 weight percent of liquid feed 102 in the aerosol 108 is removed as the drain liquid 284 in the droplet classifier 288, with preferably less than about 20 weight percent being removed and most preferably less than about 15 weight percent being removed. Minimizing the removal of liquid feed 102 from the aerosol 108 is particularly important for commercial applications to increase the yield of high quality particulate product 116.

Figure 30:
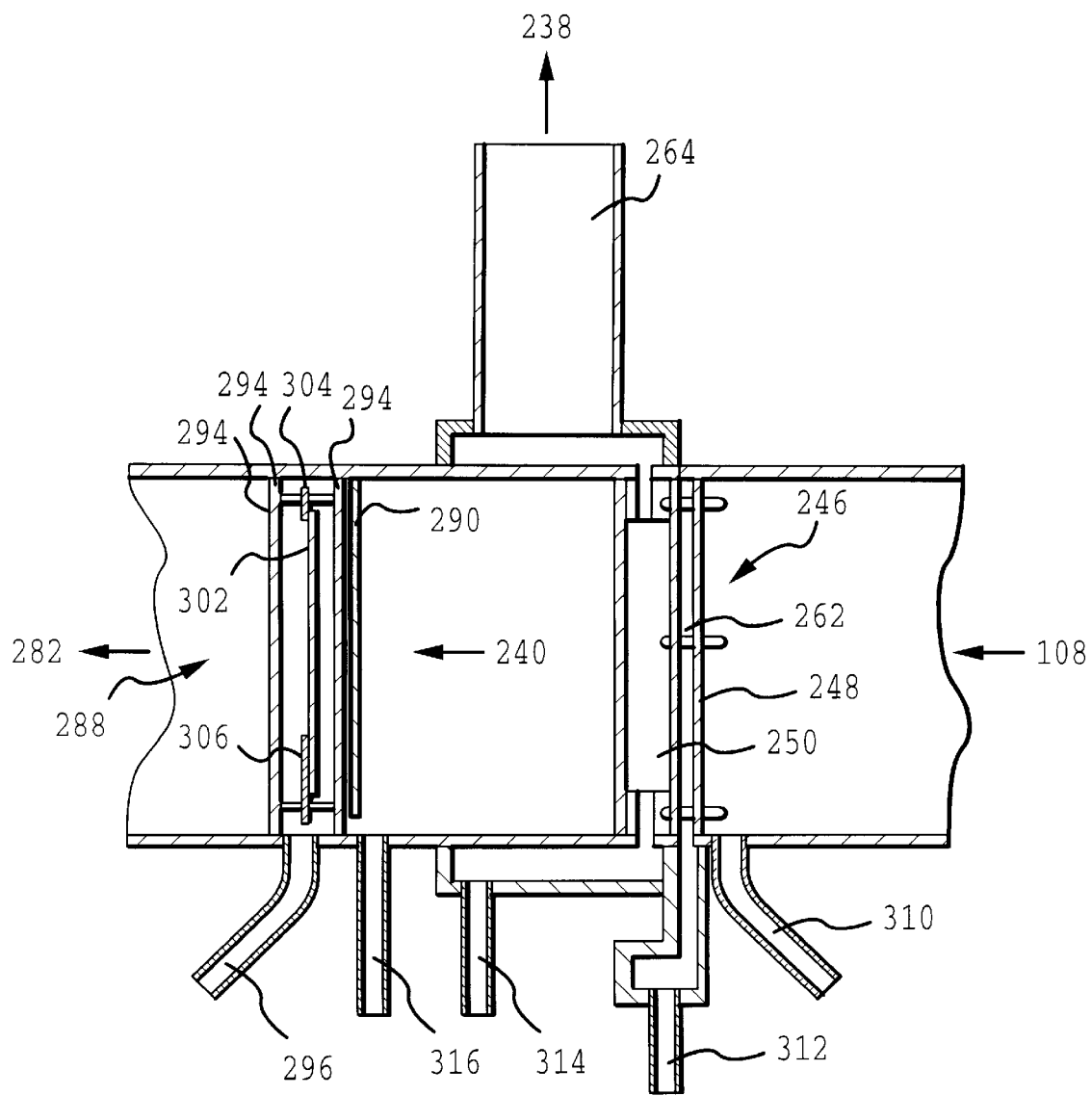
FIG. 30 shows a side view in cross section of a virtual impactor in combination with an impactor of the present invention for concentrating and classifying droplets in an aerosol.

Often times it is desirable to use both the aerosol concentrator 236 and the droplet classifier 280 to produce an extremely high quality aerosol stream for introduction into the furnace for the production of particles of highly controlled size and size distribution. Referring now to FIG. 30, one embodiment of the present invention is shown incorporating both the virtual impactor 246 and the impactor 288. Basic components of the virtual impactor 246 and the impactor 288, as shown in FIG. 30, are substantially as previously described with reference to FIGS. 16–29. As seen in FIG. 30, the aerosol 108 from the aerosol generator 106 is fed to the virtual impactor 246 where the aerosol stream is concentrated to produce the concentrated aerosol 240. The concentrated aerosol 240 is then fed to the impactor 288 to remove large droplets therefrom and produce the classified aerosol 282, which may then be fed to the furnace 210. Alternatively, the order of the aerosol concentrator and the aerosol classifier could be reversed, so that the aerosol concentrator 236 follows the aerosol classifier 280.

One important feature of the design shown in FIG. 30 is the incorporation of drains 310, 312, 314, 316 and 296 at strategic locations. These drains are extremely important for industrial-scale particle production because buildup of liquid in the process equipment can significantly impair the quality of the particulate product 116 that is produced. In that regard, drain 310 drains liquid away from the inlet side of the first plate assembly 248 of the virtual impactor 246. Drain 312 drains liquid away from the inside of the concentrating chamber 262 in the virtual impactor 246 and drain 314 removes liquid that deposits out of the excess carrier gas 238. Drain 316 removes liquid from the vicinity of the inlet side of the flow control plate 290 of the impactor, while the drain 296 removes liquid from the vicinity of the impactor plate 302. Without these drains 310, 312, 314, 316 and 296, the operation of the apparatus shown in FIG. 30 would not be satisfactory. All liquids drained in the drains 310, 312, 314, 316 and 296 may advantageously be recycled for use to prepare the liquid feed 102.

Figure 31:
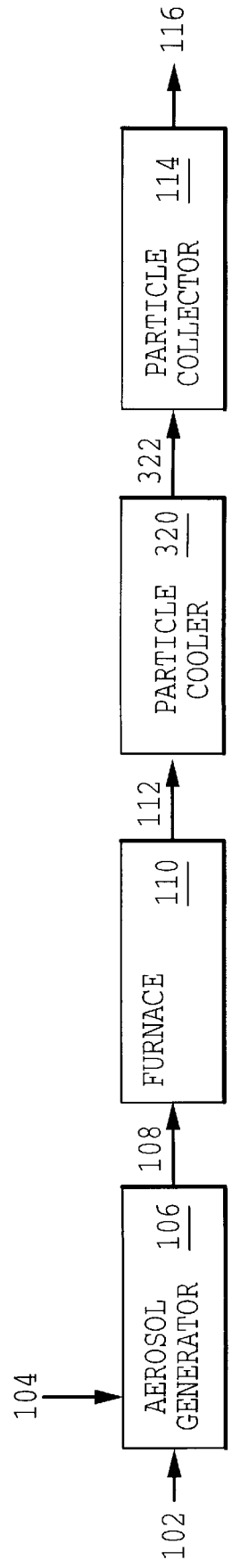
FIG. 31 is a process block diagram of one embodiment of the present invention including a particle cooler.

With some applications of the process of the present invention, it may be possible to collect the particles 112 directly from the output of the furnace 110. More often, however, it will be desirable to cool the particles 112 exiting the furnace prior to collection of the particles 112 in the particle collector 114. Referring now to FIG. 31, one embodiment of the process of the present invention is shown in which the particles 112 exiting the furnace 110 are sent to a particle cooler 320 to produce a cooled particle stream 322, which is then feed to the particle collector 114. Although the particle cooler 320 may be any cooling apparatus capable of cooling the particles 112 to the desired temperature for introduction into the particle collector 114, traditional heat exchanger designs are not preferred. This is because a traditional heat exchanger design ordinarily subjects the stream in which the particles 112 are suspended to cool surfaces. In that situation, significant losses of particles 112 occur due to thermophoretic deposition of the hot particles 112 on the cool surfaces of the heat exchanger. According to the present invention, a gas quench apparatus is provided for use as the particle cooler 320 that significantly reduces thermophoretic losses compared to a traditional heat exchanger.

Figure 32:
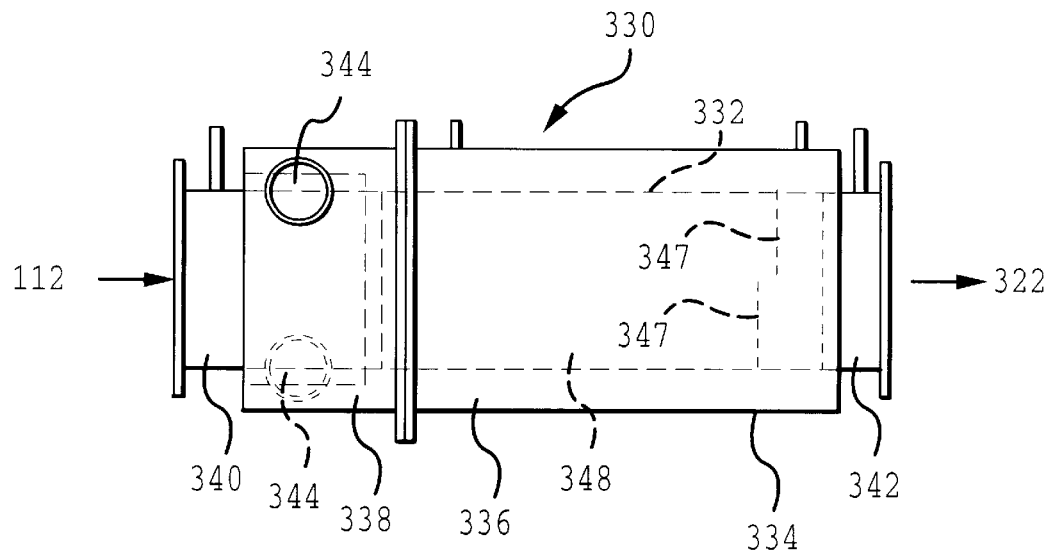
FIG. 32 is a top view of a gas quench cooler of the present invention.
Figure 33:
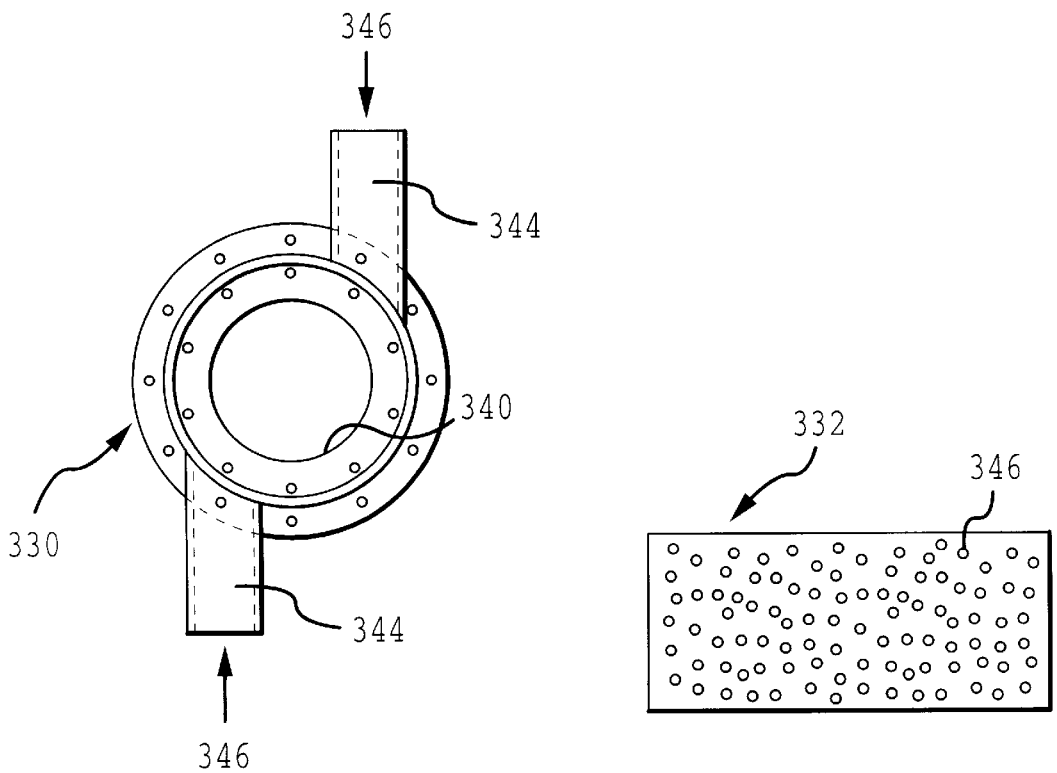
FIG. 33 is an end view of the gas quench cooler shown in FIG. 32.
Figure 34:
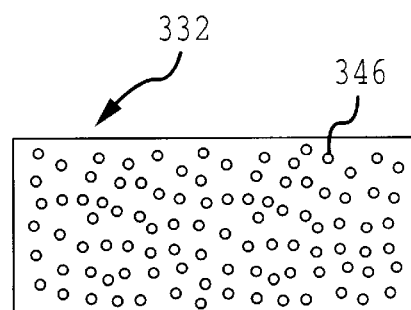
FIG. 34 is a side view of a perforated conduit of the quench cooler shown in FIG. 32.

Referring now to FIGS. 32–34, one embodiment of a gas quench cooler 330 is shown. The gas quench cooler includes a perforated conduit 332 housed inside of a cooler housing 334 with an annular space 336 located between the cooler housing 334 and the perforated conduit 332. In fluid communication with the annular space 336 is a quench gas inlet box 338, inside of which is disposed a portion of an aerosol inlet conduit 340. The perforated conduit 332 extends between the aerosol inlet conduit 340 and an aerosol outlet conduit 342. Attached to an opening into the quench gas inlet box 338 are two quench gas feed tubes 344. Referring specifically to FIG. 34, the perforated tube 332 is shown. The perforated tube 332 has a plurality of openings 345. The openings 345, when the perforated conduit 332 is assembled into the gas quench cooler 330, permits the flow of quench gas 346 from the annular space 336 into the interior space 348 of the perforated conduit 332.

With continued reference to FIGS. 32–34, operation of the gas quench cooler will now be described. During operation, the particles 112, carried by and dispersed in a gas stream, enter the gas quench cooler 330 through the aerosol inlet conduit 340 and flow into the interior space 348 of perforated conduit 332. Quench gas 346 is introduced through the quench gas feed tubes 344 into the quench gas inlet box 338. Quench gas 346 entering the quench gas inlet box 338 encounters the outer surface of the aerosol inlet conduit 340, forcing the quench gas 346 to flow, in a spiraling manner, into the annular space 336, where the quench gas 346 flows through the openings 345 through the walls of the perforated conduit 332. In this manner, the quench gas 346 enters in a radial direction into the interior space 348 of the perforated conduit 332 around the entire periphery of the perforated conduit 332 and over the entire length of the perforated conduit 332. The cool quench gas 346 mixes with and cools the hot particles 212, which then exit through the aerosol outlet conduit 342 as the cooled particle stream 322. The cooled particle stream 322 can then be sent to the particle collector 114 for particle collection.

Because of the entry of quenched gas into the interior space 348 of the perforated conduit 322 in a radial direction about the entire periphery and length of the perforated conduit 322, a buffer of the cool quench gas 346 is formed about the inner wall of the perforated conduit 332, thereby significantly inhibiting the loss of hot particles 112 due to thermophoretic deposition on the cool wall of the perforated conduit 332.

Figure 35:
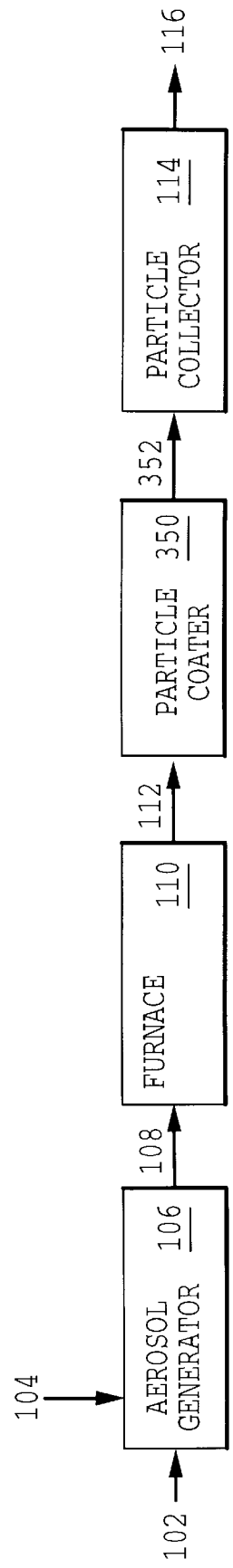
FIG. 35 is a process block diagram of one embodiment of the present invention including a particle coater.
Figure 37:
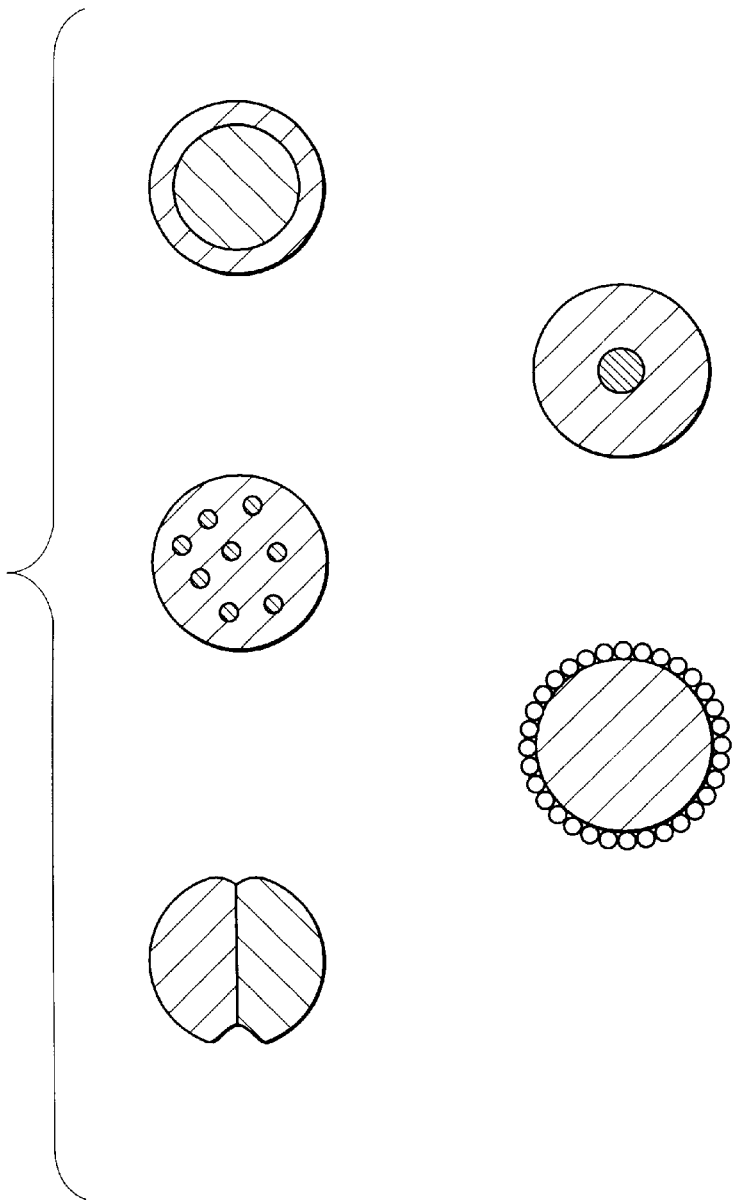
FIG. 37 shows cross sections of various particle morphologies of composite particles manufacturable according to the present invention.
Figure 38:
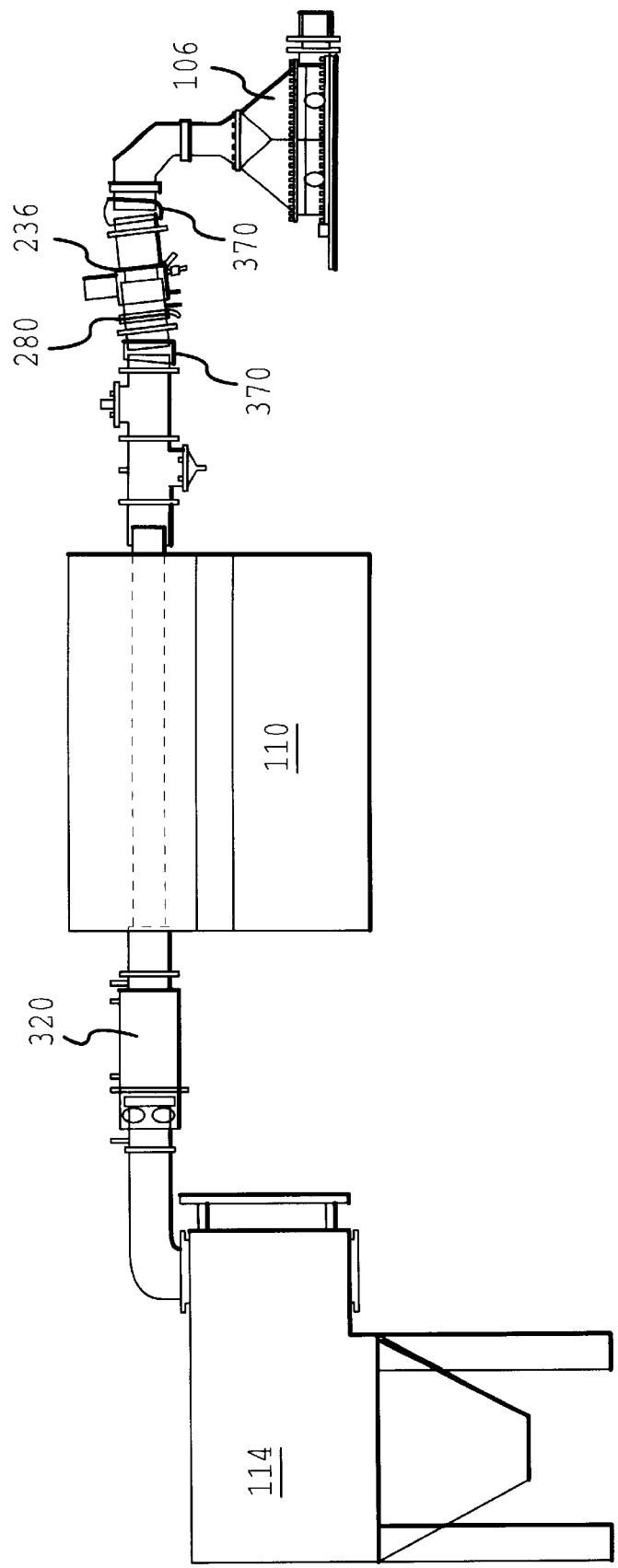
FIG. 38 shows a side view of one embodiment of apparatus of the present invention including an aerosol generator, an aerosol concentrator, a droplet classifier, a furnace, a particle cooler, and a particle collector.

In an additional embodiment, the process of the present invention can also incorporate compositional modification of the particles 112 exiting the furnace. Most commonly, the compositional modification will be to coat the particles 112 with a coating material. One embodiment of the process of the present invention incorporating particle coating is shown in FIG. 35. As shown in FIG. 35, the particles 112 exiting from the furnace 110 go to a particle coater 350 where a coating is placed over the outer surface of the particles 112 to form coated particles 352, which are then sent to the particle collector 114 for preparation of the particulate product 116.

In the particle coater, the particles 112 are coated using any suitable particle coating technology. Preferably, however, the coating is accomplished by chemical vapor deposition (CVD) or physical vapor deposition (PVD). In CVD coating, one or more vapor phase coating precursors are reacted to form a surface coating on the particles. In PVD coating, coating material, without chemical reaction, physically deposits on the surface of the particles 112. Another possible surface coating method is surface conversion of the surface portion of the articles 112 by reaction with a vapor phase reactant to convert a surface portion of the articles to a different material than that originally contained in the particles 112.

In a preferred embodiment, when the particles are coated according to the process of the present invention, the particles 112 are also manufactured via the aerosol process of the present invention, as previously described. The process of the present invention can, however, be used to coat particles that have been premanufactured by a different process, such as by a liquid precipitation route. When coating particles that have been premanufactured by a different route, such as liquid precipitation, it is preferred that the particles remain in a dispersed state from the time of manufacture to the time that the particles are introduced in slurry form into the aerosol generator 106 for preparation of the aerosol 108 to form the dry particles 112 in the furnace 110, which particles 112 can then be coated in the particle coater 350. Maintaining particles in a dispersed state from manufacture through coating avoids problems associated with agglomeration and redispersion of particles if particles must be redispersed in the liquid feed 102 for feed to the aerosol generator 106. For example, for particles originally precipitated from a liquid medium, the liquid medium containing the suspended precipitated particles could be used to form the liquid feed 102 to the aerosol generator 106. It should be noted that the particle coats could be an integral extension of the furnace 110 as could be a separate piece of equipment.

In a further embodiment of the present invention, following preparation of particles 112 in the furnace 110, the particles may be structurally modified to impart desired physical properties prior to particle collection. Referring now to FIG. 36, one embodiment of the process of the present invention is shown including such structural particle modification. The particles 112 exiting the furnace 110 go to a particle modifier 360 where the particles are structurally modified to form modified particles 362, which are then sent to the particle collector 114 for preparation of the particulate product 116. The particle modifier 360 is typically a furnace, such as an annealing furnace, which may be integral with the furnace 110 or may be a separate heating device. Regardless, it is important that the particle modifier 360 have temperature control that is independent of the furnace 110, so that the proper conditions for particle modification may be provided separate from conditions required of the furnace 110 to prepare the particles 112. The particle modifier 360, therefore, typically provides a temperature controlled environment and necessary residence time to effect the desired structural modification of the particles 112.

The structural modification that occurs in the particle modifier may be any modification to the crystalline structure or morphology of the particles 112. For example, the particles 112 may be annealed in the particle modifier to densify the particles 112 or to recrystallize the particles 112 into a polycrystalline or single crystalline form. Also, especially in the case of composite particles 112, the particles may be annealed for a sufficient time to permit redistribution within the particles 112 of different material phases.

The initial morphology of composite particles made in the furnace 110 according to the present invention could take a variety of forms, depending upon the specified materials involved and the specific processing conditions. Examples of possibly composite particles morphologies are shown in FIG. 37. These morphologies could be those initially produced in the furnace 110 or that result from structural modification in the particle modifier 360.

While various specific embodiments of the process of the present invention and the apparatus of the present invention have been described in detail, it should be recognized that the features described with respect to each embodiment may be combined, in any combination, with features described in any other embodiment, to the extent that the features are compatible. For example, any or all of the aerosol concentrator, aerosol classifier, particle cooler, particle coater and particle modifier may be incorporated into the apparatus and/or process of the present invention. Also, additional apparatus and/or process steps may be incorporated to the extent they do not substantially interfere with operation of the process of the present invention or the apparatus useful therefore. For example, to further control the size distribution of particles produced accordingly to the process of the present invention, a particle classifier could be used after particle cooling and before particle collection. Other modifications will become apparent to those skilled in the art. All such modifications are intended to be within the scope of the present invention.

Referring now to FIG. 38, an embodiment of the apparatus of the present invention is shown that includes the aerosol generator 102 (in the form of the 400 transducer array design) the aerosol concentrator 236 (in the form of a virtual impactor), a droplet classifier 280 (in the form of an impactor), the furnace 110, the particle cooler 320 (in the form of a gas quench cooler) and the particle collector 114 (in the form of a bag filter). All process equipment components are connected via appropriate flow conduits that are substantially free of sharp edges that could detrimentally cause liquid accumulations in the apparatus. Also, it should be noted that flex connectors 370 are used upstream and downstream of the aerosol concentrator 236 and the droplet classifier 280. By using the flex connectors 370, it is possible to vary the angle of slant of vertically extending slits in the aerosol concentrator 236 and/or the droplet classifier 280. In this way, a desired slant for the vertically extending slits may be set to optimize the draining characteristics off of the vertically extending slits for any particular particle manufacture operation in which the apparatus is to be used.

The aerosol generator of the present invention may have a different design depending upon the specific application. For example, when larger particles are desired, such as those above a size of about 8–10 microns, a spray nozzle atomizer may be used. For smaller-particle applications, however, and particularly for those applications to produce particles smaller than about 5 microns, an ultrasonic generator, as described herein, is preferred.

Although ultrasonic aerosol generators have been used for medical applications and home humidifiers, use of ultrasonic generators for spray pyrolysis particle manufacture has been largely confined to small-scale experimental situations.

The ultrasonic aerosol generator of the present invention described with reference to FIGS. 2–15, however, is suited for commercial applications, and especially those in which extremely high quality particles of a narrow sized distribution are desired for speciality applications. In that regard, the aerosol generator produces a high quality aerosol, with heavy droplet loading and at a high rate of production. Such a combination of narrow size distribution, heavy droplet loading, and high production rate provide significant advantages over existing aerosol generators that usually suffer from at least one of inadequately narrow sized distribution, undesirably low droplet loading, or unacceptably low production rate.

Through the careful and controlled design of the ultrasonic generator of the present invention, an aerosol having greater than about 80 weight percent of droplets in the size range of from one micron to about 10 microns may be produced. Also, the ultrasonic generator of the present invention is capable of delivering high output rates of liquid feed in the aerosol. The rate of liquid feed, at the liquid loadings previously described, is preferably greater than about 25 milliliters per hour per transducer, more preferably greater than about 37.5 milliliters per hour per transducer, even more preferably greater than about 50 milliliters per hour per transducer and most preferably greater than about 100 millimeters per hour per transducer. This high performance is required for commercial applications and is accomplished with the present invention with a relatively simple design including a single precursor bath over an array of ultrasonic transducers. For example, when the aerosol generator has a 400 transducer design, as described with reference to FIGS. 5–15, the aerosol generator is capable of producing a high quality aerosol having high droplet loading as previously described, and a total production rate of preferably greater than about 10 liters per hour of liquid feed, more preferably greater than about 15 liters per hour of liquid feed, even more preferably greater than about 20 liters per hour of liquid feed and most preferably greater than about 40 liters per hour of liquid feed.

The present invention is particularly directed to powder batches of pharmaceutically active particles having a small average particle size, for example from about 0.5 μm to about 5 μm, a narrow particle size distribution and a substantially spherical morphology. The present invention is also directed to methods for producing such powders.

The present invention is applicable to a variety of pharmaceutically-active compounds. The powders can include, but are not limited to, such pharmaceutically-active compounds as insulin, human growth hormone and similar compounds as well as steroids, proteins and peptides. Particularly preferred pharmaceutically-active compounds according to the present invention include MePhe peptides, glutathione, RGD peptide, dDAVP, renin, cyclosporine, leuprolide acetate, insulin, interferon-α, calcitonin, growth hormone, antitrypsin and albumin. The pharmaceutical particles will typically include relatively small amounts of such drug compositions, such as about 20 weight percent or less, and will include a large portion of other materials such as a matrix material (e.g. sugars), stabilizers and the like.

The pharmaceutical powders according to the present invention consist of particles having a small average size. For dry powder inhalers, it is desirable to have an aerodynamic diameter of about 2 μm. The aerodynamic diameter is defined as a particle which behaves aerodynamically like a spherical particle with a density of 1 g/cc. As a result, it is desirable that the pharmaceutical powders of the present invention have an average particle size of less than about 5 μm, preferably from about 1 μm to about 3 μm and most preferably about 2 μm, since the density of the particles is typically only slightly greater than about 1 g/cc.

According to the present invention, the pharmaceutical powder batch also has a narrow particle size distribution such that the majority of particles are substantially the same size. Preferably, at least about of 90 percent of the particles by number and more preferably at least about 95 percent of the particles by number are smaller than twice the average particle size. Thus, when the particle size is about 2 micrometer, it is preferred that at least about 90 percent of the particles are less than 4 micrometers and it is more preferred that at least of 95 percent of the particles are less than 4 micrometers. Further, it is preferred that at least about 90 percent and more preferably at least about 95 percent of the particles by number are less than about 1.5 times the average particle size. Thus, when the average particle size is about 2 micrometers, it is preferred that at least about 90 percent of the particles are less than 3 micrometers.

For some pharmaceutical powders, it may be preferable to include the pharmaceutically-active compound in substantially crystalline form as it is believed that some pharmaceutically-active compounds are biologically more effective when in a crystalline form. Therefore, it is desirable for some compositions that at least about 80 percent of the pharmaceutically-active compound in the powder batch is crystalline. However, particles can be amorphous or partially crystalline and be useful as a pharmaceutical. Varying polymorphs (different crystalline forms) are often desirable because they can have different solubilities and bioactivities.

According to one embodiment of the present invention, the pharmaceutical particles of the present invention are also substantially spherical in shape. It is believed that spherical particles are particularly advantageous because such particles will have a more consistent aerodynamic diameter, which is important for delivering the proper dosage of pharmaceutically-active compound to the user. Further, spherical particles have less tendency to agglomerate and therefore can be dispersed in a carrier gas more easily.

The pharmaceutical powders of the present invention can therefore provide a significant advantage over known powders, particularly when used in dry powder inhalers or similar devices. Presently, dry powder inhalers typically attempt to introduce an excess of pharmaceutically-active compound to the user, since lack of control over the powder morphology and size creates significant variability in the amount of the compound that effectively reaches the lungs of the user. The necessary use of excess pharmaceutically-active compounds adds significantly to the cost of the treatment. The powders of the present invention can advantageously reduce the amount of powder that the inhaler is designed to deliver since the percentage of powder that effectively reaches the lungs of the user will be increased.

A preferred method for producing the powders according to the present invention generally includes the steps of providing a solution containing pharmaceutical particle precursor materials, forming droplets from the solution, moving the droplets in a carrier gas toward a heating zone, classifying the droplets to remove droplets of a predetermined size, and passing the droplets through the heating zone to dry the liquids and form pharmaceutical particles from the droplets.

The precursor solution includes the components that will form the desired pharmaceutical particle. For example, the solution can include the pharmaceutically-active compound (e.g. insulin), a carrier matrix compound (e.g. a sugar), a buffer (e.g. glycine) and a stabilizer (e.g. sodium citrate). The solution preferably has a concentration of from about 1 to about 50 weight percent of the particle precursor components, more preferably from about 1 to about 25 weight percent and most preferably from about 1 to about 15 weight percent. The preferred solvent is water.

The precursor solution is formed into a plurality of droplets, i.e. an aerosol, using a droplet generator. The solution can be formed into droplets using nozzle systems or disk atomizers, or the like. Preferably, the solution is atomized using an ultrasonic nebulizer, such as one employing ultrasonic transducers.

In this embodiment, the transducers are disposed in relation to the solution such that the vibrational energy of the transducers can be efficiently translated to the solution, although it is not necessary that the transducers be in direct contact with the solution. It may be preferable to utilize a barrier between the transducer and the solution which is capable of transferring the vibrational energy to the precursor solution. The transducers preferably vibrate at a frequency of from about 1 MHz to about 5 MHz, more preferably from about 1.5 MHz to about 3 MHz.

The average size of the droplets produced is dependent upon a number of factors, including the transducer frequency, the density of the solution, and the concentration of precursor in the solution. Generally, the average size of the droplets decreases with increasing vibrational frequency. According to one embodiment of the present invention, the droplets have an average size of from about 1 $\mu$m to about 10 $\mu$m, more preferably from about 2 $\mu$m to about 5 $\mu$m. Ultrasonic transducers can advantageously produce a relatively high output of droplets having a small droplet size. It should be noted that some pharmaceutical compositions may be degraded by the use of an ultrasonic nebulizer. In such cases, it is preferable to use a nozzle system, such as a two fluid nozzle, to form an aerosol from the precursor solution.

A carrier gas under controlled pressure is introduced to move the droplets away from the droplet generator. The carrier gas is preferably an inert carrier gas that will not adversely react with the particles, such as nitrogen, argon or helium.

As the droplets are formed and carried away by the carrier gas, the solution will begin to concentrate over time. Therefore, precursor solution is constantly recirculated to maintain a substantially constant concentration of the precursor materials. If the concentration of the precursors increases too greatly, the average droplet size can increase to an undesirable level and the solution can become difficult to nebulize. Additional, solvent, for example water, can also be added to the solution to replace solvent lost by vaporization during droplet generation.

The carrier gas is adapted to move the droplets in aerosol form to a heating zone wherein the particles are heated to dry the solvent and form solid pharmaceutical particles. According to a preferred embodiment of the present invention, the droplets are classified prior to entering the heating zone to remove droplets having a size greater than a maximum size. In a preferred embodiment, droplets having a size of greater than about 10 $\mu$m are removed from the aerosol, more and more preferably droplets having a size of greater than about 8 $\mu$m are removed.

Droplets having a size greater than a maximum size can be removed from the droplet stream by a number of methods, including a cyclone, or a settling chamber. In a preferred embodiment, the larger droplets are removed using an impactor, such as a slit impactor or an inertial impactor. Preferably, an inertial impactor is used to remove the large droplets. An inertial impactor utilizes a wall that is situated in the path of the flowing carrier gas. The wall has a gap or hole at an end that is spaced from the center of the wall. Small particles, with lower inertia, flow with the carrier gas through the gap. Larger particles impact upon the wall and are thereby removed from the carrier gas stream. The larger particles, now in the form of a liquid stream, flow down the impactor wall and the resultant solution can advantageously be recycled to conserve the pharmaceutical.

In addition to removing maximum size droplets, it can also be advantageous to remove minimum size droplets from the carrier gas stream Preferably, minimum size droplets are removed from the carrier gas stream using a virtual impactor. A virtual impactor also uses inertial forces to separate the droplets. The carrier gas stream enters the virtual impactor and is passed through a first aperture. Opposite the first aperture is a second aperture located directly across from the first aperture. A portion of the carrier gas is removed from the normal flow path by the virtual impactor. Preferably a majority of the gas from the carrier gas stream is removed and the removed gas carries with it all droplets having insufficient inertia, i.e. small enough size, to be carried out of the path of the second aperture. Droplets above a minimum size continue in a substantially straight path through the second aperture.

In addition to removing smaller droplets and thereby narrowing the size distribution of droplets, the virtual impactor advantageously removes a majority of the carrier gas thereby concentrating the droplets in the carrier gas stream and resulting in higher production rates. The use of a virtual impactor or a similar device also removes moisture from the gas stream during production of the particles which advantageously reduces agglomeration of the powder after dispersion of the powder into the aerosol phase for inhalation. The virtual impactor permits the use of greater amounts of dry air than can be economically achieved in conventional spray dryers. The increased amount of dry air will advantageously permit lower drying rates since less hot gas must be added to the aerosol stream to dry the particles.

The carrier gas stream containing the classified precursor droplets is then transported to a heating zone. The heating zone is adapted to heat the droplets to a sufficient temperature for a sufficient time to evaporate the liquids and form dry solid particles from the precursor components. Preferably, the heating zone is an elongate tube that is heated to form a hot zone within the tube. The heating can be achieved by any means known in the art, such as electrical resistance heating or the like. The heating zone has a sufficient volume such that significant particle interaction is avoided. Preferably, the peak temperature within the heating zone is from about 100° C. to about 300° C., more preferably from about 100° C. to about 200° C. The total residence time in the heating zone is preferably from about 0.1 seconds to about 10 seconds, more preferably from about 1 seconds to about 5 seconds.

It is also believed that the heating rate of the droplets should be controlled since the heating rate can influence the rugosity of the particle. Rugosity is the surface area of the actual particle relative to the surface area of perfect spheres of the same mass. It is believed that for most applications, pharmaceutical particles having lower rugosity are desirable. Lower rugosity particles will disperse from dry powder into an aerosol for inhalation better than particles having a high rugosity. The heating rate can also influence the crystallinity of the pharmaceutically-active compound.

It is therefore believed that lower heating rates are preferred. For example, a heating rate of from about 10° C. to about 50° C. per second maybe preferred for some pharmaceutical compounds, although some compounds be heated at rates as high as 100° C. per second. The heating rate can be controlled by controlling the temperature in the axial direction along the flow path or by introducing dry air through the walls along the length of the tube to control the drying rate.

The thus-formed pharmaceutical particles exit the heating zone and are separated from the carrier gas.

According to one embodiment of the present invention it is preferred to mix the pharmaceutical particles with excipient particles which are larger particles that enhance the redispersion of the pharmaceutical powder into a gas before inhalation. According to the present invention, it is possible to mix the excipient particles, such as lactose, maltose or surcrose, with the pharmaceutical particles before collection in a filter to give more homogenous mixing of the pharmaceutical particles and the excipient particles. The increased mixing will lead to better dispersion of the powder into a suspended phase in the inhaler device.

After being collected, the powder is preferably placed into packets such that the powder can be redispersed into a gas inhaled in an inhalation device.

The surfaces of the pharmaceutical particles according to the present invention can also be modified, for example while the particles are in the gas phase. Surface coatings can be used to modify the hydrophilicity, hydrophobicity or charging of the particle surface, for example to reduce particle agglomeration. A surface coating can be applied by condensing a vapor onto the surfaces of the pharmaceutical particles or by reacting a vapor with the surface of the particles before collection. The particles can also be coated after being collected. Coatings can include organic compounds such as sugars or inorganic compounds such as metal carboxylates.

In another embodiment of the present invention, it is preferred to form a composite of the foregoing pharmaceutical compounds with an inorganic material having a higher density than the pharmaceutical particles. The composite particles will then have a higher density and can therefore redisperse more easily into the gas stream in the inhaler device. The higher density material can include oxides such as alumina, titania, silica, boehmite, iron oxides or the like. The composite particles can be formed by, for example, dispersing colloids of higher density materials in the precursor solution. The colloids will suspend within the droplets formed by the nebulizer and will be dispersed throughout the particle.

EXAMPLE

Mannitol is a sugar that is a common matrix material for the production of solid pharmaceutical powders, such as insulin powders.

Mannitol particles were formed in the following manner. An aqueous solution was prepared by adding 10 grams of mannitol to 100 ml of water to yield a concentration of mannitol in solution of about 10 weight percent. The solution was placed in an ultrasonic nebulizer and the ultrasonic transducers were run at a frequency of 1.6 MHz producing an aerosol of mannitol solution.

A carrier gas comprising nitrogen was introduced at a flow rate of about 30 liters per minute to move the droplets toward a heating zone. Prior to entering the heating zone, the aerosol moved through an impactor set to remove particles having an aerodynamic diameter of greater than about 10 µm. At the heating zone inlet, an additional 150 liters per minute of dry air is added. The aerosol stream then entered the heating zone which was an elongate ceramic tube heated to a peak temperature of about 200° C. The liquid evaporated in the tube and mannitol particles were collected at the opposite end of the tube.

The mannitol particles were substantially spherical when observed under a scanning electron microscope and had an average particle size of about 2 µm and a very narrow particle size distribution.

While various embodiments of the present invention have been described in detail, it is apparent that modifications and adaptations of those embodiments will occur to those skilled in the art. However, it is to be expressly understood that such modifications and adaptations are within the spirit and scope of the present invention.

What is claimed is:

1. A method for making a powder batch comprising a plurality of pharmaceutically-active particles, comprising the steps of:

(a) providing a solution comprising pharmaceutically-active particle precursors;

(b) forming said solution into a plurality of droplets;

(c) suspending said droplets in a carrier gas selected from the group consisting of nitrogen, argon and helium;

(d) classifying said droplets to remove substantially all droplets having a size greater than a predetermined size; and (e) heating said droplets at a temperature sufficient to remove liquids from said droplets and produce a substantially dry pharmaceutical powder batch wherein said pharmaceutically active particles are selected from the group consisting of MePhe peptides, glutathione, RGD peptides, dDAVP, renin, cyclosporine, leuprolide acetate, insulin, interferon-α, calcitonin, growth hormone, antitrypsin and albumin.

2. A method for making a powder batch as recited in claim 1, wherein the concentration of precursor in said solution is less than about 25 percent.

3. A method for making a powder batch as recited in claim 1, wherein said step of forming solution droplets comprises contacting said solution with transducers at a frequency of from about 1.6 MHz to about 2.4 MHz.

4. A method for making a powder batch as recited in claim 1, wherein said classifying step comprises passing said solution droplets through an impactor.

5. A method for making a powder batch as recited in claim 4, wherein said classifying step further comprises subjecting said solution droplets to a virtual impactor.

6. A method for making a powder batch as recited in claim 1, wherein said heating step comprises heating said droplets to a temperature of from about 100° C. to about 300° C.

7. A method for making a powder batch as recited in claim 6, wherein said heating step further comprises passing said droplets through an elongate heating zone.

* * * * *

UNITED STATES PATENT AND TRADEMARK OFFICE
CERTIFICATE OF CORRECTION

PATENT NO. : 6,051,257
DATED : April 18, 2000
INVENTOR(S) : Hampden-Smith et al.

It is certified that error appears in the above-identified patent and that said Letters Patent is hereby corrected as shown below:

<u>Column 1,</u>
Line 12, insert the following paragraph:
-- STATEMENT REGARDING FEDERALLY-SPONSORED RESEARCH/ DEVELOPMENT
This invention was made with Government support under contracts N00014-95-C-0278 and N00014-96-C-0395 awarded by the Office of Naval Research. The Government has certain rights in the invention. --

Signed and Sealed this

Fifth Day of April, 2005

JON W. DUDAS
*Director of the United States Patent and Trademark Office*